(12) United States Patent
Koehl et al.

(10) Patent No.: US 8,626,524 B1
(45) Date of Patent: Jan. 7, 2014

(54) SYSTEM AND METHOD FOR TRANSFERRING DATA WITH ELECTRONIC MESSAGES

(75) Inventors: John Koehl, Hamilton, OH (US); Sudheendra V. Galgali, Mason, OH (US); Wendy A. Neu, Cincinnati, OH (US); William J. Wynne, Brookville, IN (US)

(73) Assignee: Quest Diagnostics Investments Inc., Wilmington, DE (US)

( * ) Notice: Subject to any disclaimer, the term of this patent is extended or adjusted under 35 U.S.C. 154(b) by 1971 days.

(21) Appl. No.: 11/323,980

(22) Filed: Dec. 29, 2005

(51) Int. Cl.
*G06Q 50/00* (2012.01)

(52) U.S. Cl.
USPC .................................................. 705/2

(58) Field of Classification Search
USPC ..................................... 705/2, 4, 3
See application file for complete search history.

(56) References Cited

U.S. PATENT DOCUMENTS

| | | | |
|---|---|---|---|
| 6,263,330 B1 * | 7/2001 | Bessette | 707/4 |
| 6,272,468 B1 * | 8/2001 | Melrose | 705/2 |
| 2001/0041991 A1 * | 11/2001 | Segal et al. | 705/3 |

* cited by examiner

*Primary Examiner* — John Pauls
(74) *Attorney, Agent, or Firm* — Jon E. Gordon; Frommer Lawrence & Haug LLP

(57) ABSTRACT

The invention relates to sharing patient care information through electronic messaging. Systems for managing electronic health records may comprise extensive patient information, e.g., names, addresses, insurance coverage and/or other financial arrangements, health conditions, allergies, procedures undergone, and/or tests performed. The invention involves transfer of such information between users. Embodiments of the invention may pass such information by adding to electronic messages pointers that uniquely refer to one or more patient records. Some embodiments may thereby send health information electronically while preserving metadata and/or other meaning associated with the data.

18 Claims, 16 Drawing Sheets

```
<message>
    <header>                                              866
        <sender-id>8675309069</sender-id>                 868
        <recipient-id>7365000422</recipient-id>
870     <message-id>000497521336</message-id>
        <subject>Patient Referral</subject>
864
        .
        .
        .
    </header>
    <body>
        <text>Dear Dr. Thomas: I have referred to you the patient
874     we spoke of last week. I have attached the test results to this message
        for your review. Please call me when you have time to discuss this.</text>
    </body>
    <attachments>                                         884
        <attachment type="reference">
880         60e79772bade4foc                              882
        </attachment>
    </attachments>
    .
    .
    .
</message>
```

FIG. 14

SYSTEM AND METHOD FOR TRANSFERRING DATA WITH ELECTRONIC MESSAGES

COPYRIGHT NOTICE

A portion of the disclosure of this patent document contains material that is subject to copyright protection. The copyright owner has no objection to the facsimile reproduction by anyone of the patent document or the patent disclosure as it appears in the Patent and Trademark Office patent files or records, but otherwise reserves all copyrights whatsoever.

CROSS-REFERENCE TO RELATED APPLICATIONS

This application is related to the U.S. patent application Ser. No. 11/112,696, filed Apr. 21, 2005, and entitled "SYSTEMS AND METHODS FOR ADMINISTRATION OF PRESCRIPTION DRUG BENEFITS," which is incorporated herein by reference in its entirety. This application is also related to the U.S. patent application filed on the same date herewith and entitled "GRAPHICAL PRESENTATION OF MEDICAL DATA," which is incorporated herein in its entirety.

BACKGROUND

Electronic Messaging

The present invention relates to the use of electronic messages to transfer data. More particularly, it involves the transfer of data in electronic messages with no loss of semantic data and/or other metadata or other meaning associated with the data, with application to the transfer of medical data.

Electronic messaging comprises the use of computerized services to send and receive electronic data, which may comprise, e.g., text, audio, video, and/or other electronic data.

Many forms of electronic messaging are well known, e.g., electronic mail (or email) and instant messaging. For example, depending on the system, email may comprise a system for sending asynchronous messages to one or more users. Again depending on the system, an email message may comprise a title or subject, a body that primarily comprises text, and/or one or more attachments, which may comprise computer files and/or other electronic data.

According to the prior art, an attachment to an electronic message is often a computer file. Attaching the file comprises including a representation of the entire contents of the file and descriptive data in the representation of the electronic message. When the electronic message is received, the attachment may be extracted and possibly saved as a new file by the recipient.

In some instances, a sender may itself be a computer program or system. For example, a computer may be configured to periodically transfer a log as an electronic message. Such a message may be composed and transferred without human intervention.

The transport and representation of electronic messages as email across the Internet 7 are well known and described in publicly-available Internet standards, which are called Requests for Comment ("RFCs"). Relevant RFCs comprise RFC2822 (available at http://www.ietf.org/rfc/rfc2822.txt), RFC2045 (available at http://www.ietf.org/rfc/rfc2045.txt), RFC2046 (available at http://www.ietf.org/rfc/rfc2046.txt), RFC2047 (available at http://www.ietf.org/rfc/rfc2047.txt), RFC2048 (available at http://www.ietf.org/rfc/rfc2048.txt), and RFC2049 (available at http://www.ietf.org/rfc/rfc2049.txt), among others. Other ways to represent and/or transport electronic messages are also well known. As described in these RFCs, the representation of an electronic message comprises representations of the message and the content of any attachments.

Electronic Health Records

A number of things have driven the growth in all aspects of the health care industry of computerized systems providing Electronic Health Records (EHRs) and Electronic Medical Records (EMRs). (The term "EHR system" is used herein to refer to any computerized system that may store, maintain, and/or provide EHRs. This term may have other significance in other contexts.) For example, governmental regulation continues to move towards impelling the adoption of EHR systems. In addition, EHR systems reduce the chances of loss of patient records and mistakes in data entry and make delivery of health care more efficient, thereby offering the prospects of improving patient care while lowering its cost. Further, EHR systems may help ease the burden of paperwork that now afflicts the delivery of health care.

An EHR system may record and aggregate any type of data associated with health care, including, e.g., data about patients, including, e.g., their names, addresses, insurance coverage and/or other financial arrangements, health conditions, allergies, procedures undergone, and/or tests performed. Other recorded data may relate to, among other things, health care providers, payers, pharmacies, and/or employers.

Electronic data of any sort is often associated with other data that describes it, provides context for it, associates it with other data, and/or otherwise signifies the meaning, significance, and/or one or more other attributes of the electronic data. This accompanying data is often called "metadata."

For example, in the medical field, an application may display the results of a blood test for cholesterol levels. The display may include data such as the levels of total cholesterol, HDLs, and LDLs, among other data. Some or all of this data may be associated with further data, such as the date of the test, the location where the blood sample was drawn, the identity of the laboratory ("lab") that analyzed the sample, the identity of the patient, and the identity of the practitioner who ordered the test, and this further data can be considered metadata. The appropriate characterization of data sometimes depends on the ways in which it is treated in computerized files, applications, and/or systems.

A health care provider may wish to transfer data, contained in an EHR system, about one or more patients, to other providers, for example, in connection with a medical consultation.

BRIEF SUMMARY

According to embodiments of the invention, data may be attached to an electronic message in the form of a reference that uniquely specifies a particular set of data, rather than including the data itself in the message. On receipt, the reference may be used to retrieve the attached data from a store for delivery to the recipient. For example, a computer file may be specified by a reference that comprises the name of a server and the path to the file on the server. When the recipient opens or views the message, the recipient's computer system may then contact the named server and request delivery of the specified file.

An embodiment of the invention may alternatively use a reference to specify a set of data that is not a file. For example, a reference may specify a record or set of related records in a database. In a relational database management system, such as is well known, a record may exist as a row in a table or as linked rows in one or more tables. A primary key uniquely specifies a row, and an embodiment of the invention may therefore use a primary key as the reference. Alternatively, an embodiment may generate a unique identification code for use as a reference and then associate the code with the primary key of the attached data. An embodiment of the invention may also support association of more than one primary key with a single identification code, causing the system to provide multiple records when presented with the identification code.

Similar techniques are applicable to other sorts of databases, such as object-oriented databases.

When used to identify a set of data, a reference may specify structured data sets of varying complexity. For example, an application related to electronic commerce may in some contexts treat a customer's order as a single, atomic entity, even though the data associated with the order is stored in multiple records in a database. (Such a contextual entity is sometimes referred to herein as a "data item.") But that same application may in other contexts treat the same order as a composite entity, comprising, e.g., a customer, a payment, a shipper, and one or more ordered items, each of which may itself be considered a data item in this context. These other data items may themselves be regarded in other contexts as composites that comprise more primitive data items, and so on. (The term "hierarchical data item" is intended to refer to data items that may also be considered as composites of more primitive data items.)

A reference may point to data that is associated with other data that indicates meaning, context, or both. This other data (referred to herein as "semantic data"), may, e.g., indicate that a particular value is a price or quantity, has a particular data type, and a computer application may rely on such semantic data to be able to process the data automatically. Semantic data may be explicit, such as an explicit specification of a data type, which is linked to data. Semantic data may also be implicit: the meaning of a set of values may sometimes be inferred from the database table in which they are found. Depending on the embodiment of the invention, a reference in an electronic message may refer to data in its original context of semantic data and support access to such semantic data by the recipient of the message.

In an embodiment of the invention, data is transferred via an electronic message that encodes a unique reference to some or all of the data. In an embodiment of the invention, sending data with an electronic message involves attaching to the electronic message unique references to one or more records that comprise the data. In a further embodiment of the invention, when the recipient saves a persistent copy of the received data, the database records that contain the data are duplicated, and further manipulation of the received data by the recipient involves the persistent copy of the data.

In an embodiment of the invention, data associated with semantic data may be transferred and/or duplicated by receiving an electronic message that comprises at least one reference that uniquely specifies a set of data, wherein the set of data comprises one or more original data items that are associated with semantic data; presenting the electronic message to a recipient at a first computer system; in response to input to the first computer system, presenting at the first computer system some or all of the data comprised by the set of data; and, in response to further input to the first computer system, creating a persistent copy of some or all of the data comprised by the set of data; wherein creating a persistent copy comprises creating a persistent copy of at least one of the one or more original data items that are associated with semantic data, such that each copy of a data item is associated with the same semantic data that the corresponding original data item is associated with.

In an embodiment of the invention, data associated with semantic data may be transferred and/or duplicated by receiving an electronic message that comprises at least one reference that uniquely specifies a hierarchical data item that comprises a plurality of data items; presenting the electronic message to a recipient at a first computer system; presenting to the recipient at the first computer system a user interface that comprises a display of a plurality of the plurality of data items comprised by the hierarchical data item and user interface components supporting individual selection of each data item; in response to input to the first computer system, selecting one or more of the displayed data items; and in response to further input to the first computer system, creating a persistent copy of each selected data item. In another embodiment of the invention, a reference may uniquely specify a collection of one or more hierarchical data items that each comprise a plurality of data items.

An embodiment of the invention may be implemented in association with a computerized EHR system that comprises, among other patient care features, electronic lab test ordering, online delivery and viewing of lab results, and electronic eligibility checking and prescribing. An EHR system in association with which an embodiment of the invention can be implemented may provide patient care features that support some or all of a set of tasks comprising, among others:

ordering lab tests;

accessing and viewing lab results;

providing clinical insights at the time of ordering, delivering results, or both;

preparing and ordering drug prescriptions;

performing Pharmacy Benefit Manager (PBM) eligibility checks, including pharmacy coverage, PBM formulary, and patient medication history;

performing drug-to-drug interaction checking per prescription, as well as across a patient's active medications and medication history;

performing drug-to-allergy interaction checking per prescription;

communicating prescriptions to pharmacies and/or receiving requests from pharmacies for prescription refills.

managing clinical documents received from external systems;

communicating clinical data securely within and between physician offices;

viewing data by patient, user, and organization;

analyzing patient data using various tools, including flowsheets, graphs, and informatics queries;

accessing a user-configurable inbox for both clinical and non-clinical data;

maintaining associations of physicians-to-provider organizations, physicians-to-payer plans, and physicians-to-specialties;

communicating with one or more labs to gain assistance in interpreting results;

communicating with one or more labs to order supplies; and accessing information provided by one or more labs, such information comprising, for example, test dictionaries, lab manuals, and Patient Service Center (PSC) locations.

Such an EHR system may enable access to clinical data for patients in locations that may comprise a provider's office, a hospital, and a provider's or patient's home and may provide encryption of data passed over networks comprising, for example, intranets or the Internet.

Embodiments of the invention provide facilities for transferring electronic messages that have medical data attached. The transfer of data is done with no loss of metadata.

For example, a physician using an EHR system may have electronic charts in the EHR system for one or more patients. Possibly in connection with referring a patient to another physician, the first physician desires to send data from the patient's chart to another physician who also uses the EHR system. Using the EHR system, the first physician creates an electronic message, selects and attaches the desired data, and then sends the electronic message. On delivery, the recipient can read the message, view the attached data, and, if desired, save some of all of the attached data to the recipient's own copy of the patient's chart.

Depending on the embodiment of the invention, the sender of a message may attach any data that a patient's chart contains within the EHR system. Such data may comprise, e.g., one or more of the patient's medical conditions, lab tests ordered for the patient and their results, drug prescriptions, and other data typically found in health or medical records, whether electronic or otherwise.

In an embodiment of the invention, sending data from a patient's chart with an electronic message involves attaching to the electronic message unique references to one or more database records that contain the data. In a further embodiment of the invention, when the recipient saves received data to the recipient's chart for a patient, the database record or records that contain the data are duplicated, and a reference or references to the duplicate records are stored in the recipient's copy of the patient's chart.

In an embodiment of the invention, if the recipient of an electronic message containing patient data does not have a chart for that patient, the recipient may create such a chart before adding the received patient data to it.

BRIEF DESCRIPTION OF THE DRAWINGS

The invention is illustrated in the figures of the accompanying drawings, which are meant to be exemplary and not limiting, and in which like references are intended to refer to like or corresponding things.

FIG. 4 depicts a user interface display adapted to search for a particular patient.

FIG. 9 depicts a user interface display adapted to creation of a new prescription according to an embodiment of the invention.

FIG. 11 depicts a user interface display that presents results of laboratory tests.

FIG. 14 is an example of a partial representation of an electronic message as XML according to an embodiment of the invention.

DETAILED DESCRIPTION OF THE PREFERRED EMBODIMENTS

Electronic Messaging

Figure 1A:
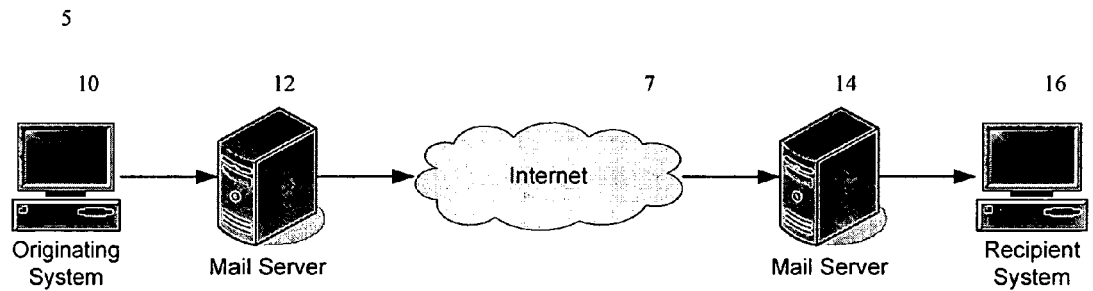
FIGS. 1a and 1b schematically depict networked computer systems suitable for implementing electronic messaging according to the prior art.

FIG. 1a depicts an example, according to the prior art, of an architecture 5 suitable for use in transferring email using the Internet 7. A sender (not pictured) interacts with an originating system 10 to compose an electronic message. Such interaction may take place, for example, through an email application such as Eudora® or Outlook®, or through a web browser, such as Firefox™ or Safari™, that interacts with an email service such as GMail™ or Yahoo!® Mail.

When it is desired to send an electronic message, the message may be sent from the originating system 10 to an email server 12. In connection with email sent via the Internet 7, the email server 12 locates the email server 14 associated with each recipient (not pictured) and transfers the message via the Internet 7. The recipient then interacts with the recipient system 16 to receive electronic messages from the email server 14. The recipient's interaction with the recipient system 16 may take place similarly to the sender's interaction with the originating system 10.

Figure 1B:
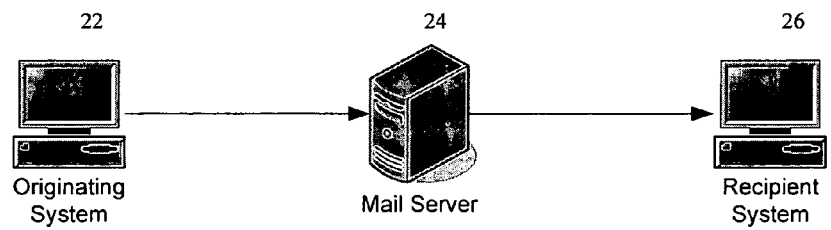

FIG. 1b depicts an alternative architecture 20, according to the prior art, that is also suitable for use in transferring electronic messages. As discussed in connection with FIG. 1a, above, a sender (not pictured) interacts with an originating system 22 to compose an electronic message. When it is desired to send the message, the message may be transferred from the originating system 22 to a mail server 24. The recipient (not pictured) interacts with the recipient system 26 to receive the email from the mail server 24.

The architectures depicted in FIGS. 1a and 1b may be combined in certain electronic messaging systems. For example, when one user of an Internet service provider ("ISP") (not pictured) sends a message to another user of the same ISP, the message may be transferred through an architecture 20 such as depicted in FIG. 1b. When that same user sends a message to a user of a different ISP, however, the message may be transferred through an architecture 5 such as depicted in FIG. 1a.

Figure 1C:
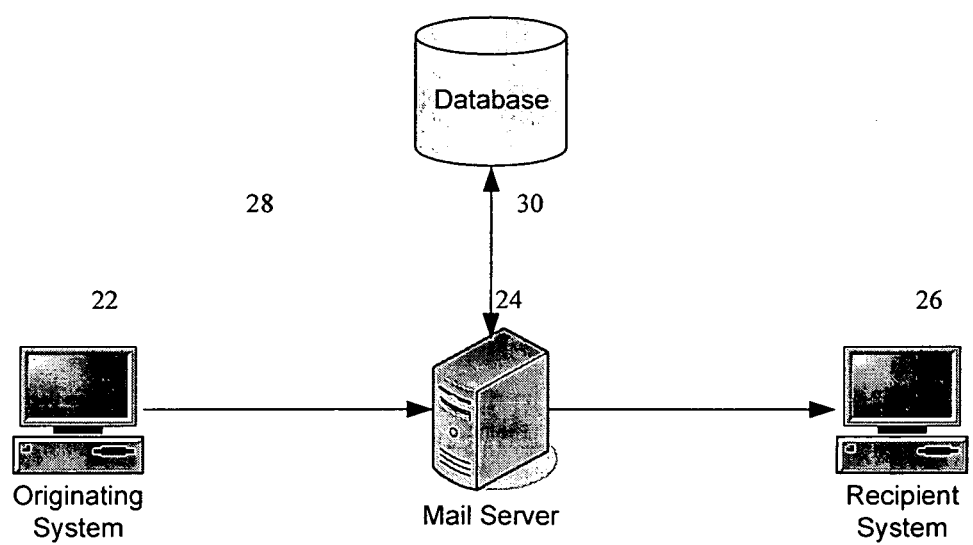
FIG. 1c schematically depicts networked computer systems suitable for implementing electronic messaging according to the invention.

FIG. 1c depicts one possible architecture 28 (of many) upon which embodiments of the invention may exist. As in the architecture depicted in FIG. 1b, a sender (not pictured) interacts with an originating system 22 to compose an electronic message. When it is desired to send the message, the message may be transferred from the originating system 22 to a mail server 24. The recipient (not pictured) interacts with the recipient system 26 to receive the email from the mail server 24.

The mail server 24 is in communication with a database 30. A database may contain one or more records, and one or more identifiers may uniquely identify a record within a database. For example, relational database management systems, in which data are represented in tabular form, are well known. A record in such a table may be represented as a row, and a value called a "primary key" may uniquely identify each row within that table.

It is well known that complex data sets and data structures may be represented by including in a row one or more references to other rows in the same and/or other tables. Associations between data sets may be represented in the same way. Such an association may, for example, link data with relevant metadata.

The nature of the data store and the reference will depend on the embodiment of the invention. The data store need not be a database 30, as depicted in FIG. 1c, or a file server, but may be any store of electronic data from which a unique reference to data may be used to retrieve that data. For instance, the data store may be part of a distributed object-oriented application, and the reference may be a unique object reference within the system.

The data store need not be in direct communication with the mail server 24, as depicted in FIG. 1c. For example, the originating system 22 may insert a unique reference to electronic data into an electronic message. On receipt, the recipient system 26 may then use that reference to retrieve the referred-to data from a data store.

It will be appreciated by those skilled in the art that the architectures depicted in FIGS. 1a-1c are just a few of many suitable for the described implementations. More than one component may be involved in performing one or more of the functions of the system, depending on the expected load and other factors. Functions depicted as being performed by separate components may in some implementations be performed by a single component, again, depending on the expected load and other needs of the system. Other configurations of servers and network topologies may work as well as those described here.

EHR Architecture

In the discussion that follows, the invention is discussed in connection with EHR systems. Such discussion is meant to illustrate the invention with respect to certain preferred embodiments, but it is to be understood that the discussion is illustrative and not limiting. It will be appreciated by one skilled in the art that electronic messaging according to the invention may transfer any sort of electronic data by reference, not just medical or health-related data, and not only in connection with EHR systems.

Figure 2:
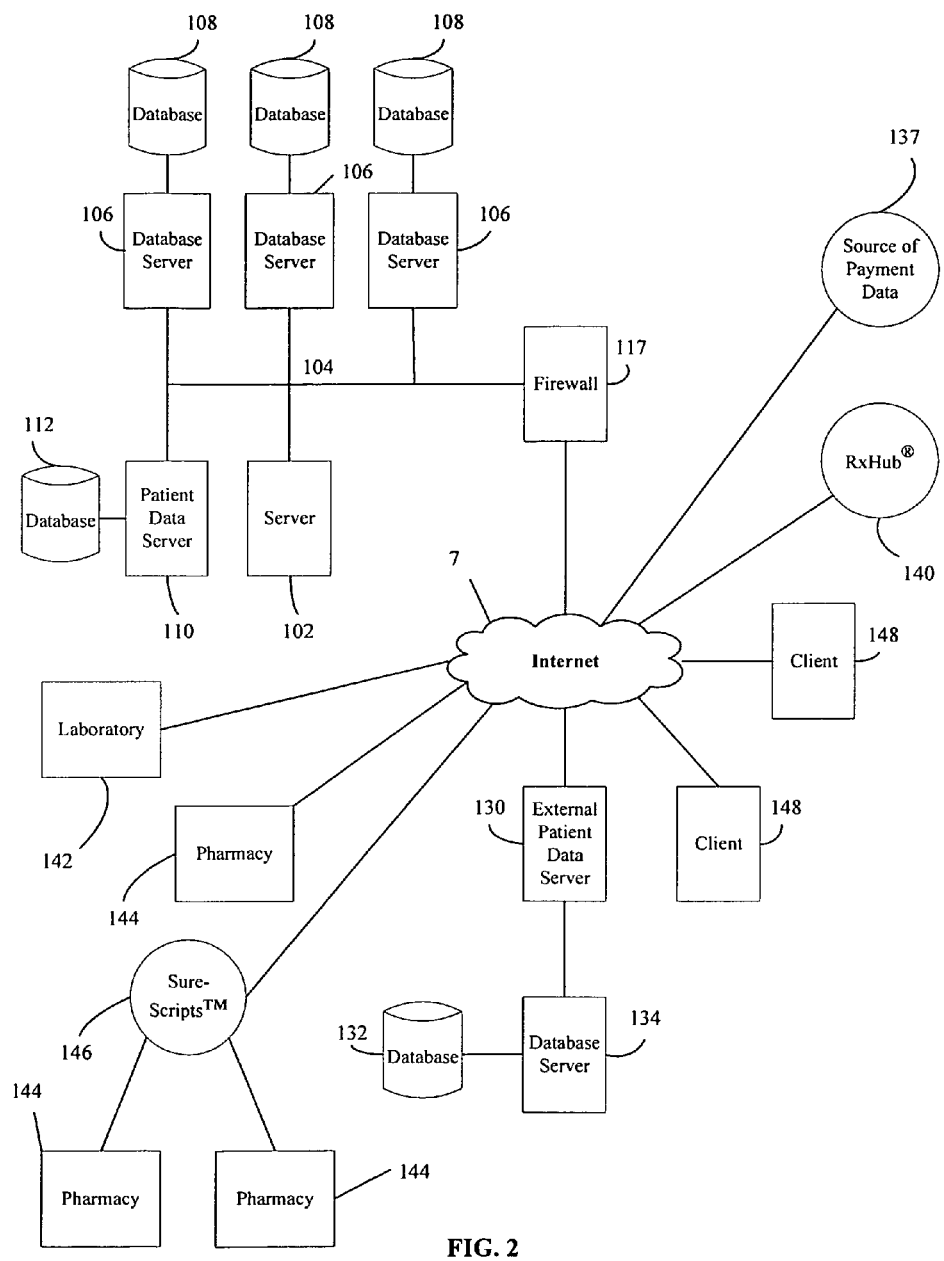
FIG. 2 schematically depicts networked computer systems suitable for implementing the invention.

FIG. 2 depicts an example of an architecture 100 suitable for use with an EHR system.

An EHR system itself may comprise computer software, software components, or both, executing on one or more servers 102. One or more interconnected local area networks 104 may connect the server 102 to one or more database servers 106, each of which provides access to one or more databases 108. The local area network may also contain one or more systems 110 that provide access to patients' medical histories, which may be stored in one or more local databases 112.

In the architecture depicted in FIG. 2, communication with other sources and consumers of information is achieved using the Internet 7. Access to the Internet may optionally be through one or more firewalls, gateways, and/or other security arrangements 117. Other means of communication may also be used instead of or in addition to the Internet, such as dial-up lines, dedicated leased lines, and private wide area networks (not pictured).

As depicted in FIG. 2, patient medical data may be stored in one or more databases 108, 112 and/or may be obtained from one or more external sources, such as server 130, which itself has access to a database 132 through a database server 134.

Information about health insurance and other forms of payment may be received electronically from one or more sources 137. Prescription insurance data, which may comprise formulary data and rules, may also be received electronically from one or more sources, such as RxHub® 140.

An EHR system may be connected to one or more medical laboratories 142. Similarly, an EHR system may be connected to one or more pharmacies 144, directly and/or through a prescribing hub such as SureScripts™ 146.

Access to the EHR system is by one or more clients 148.

It will be appreciated by those skilled in the art that the architecture depicted in FIG. 2 is just one of many suitable for implementation of the invention. More than one component may be involved in performing one or more of the functions of the system, depending on the expected load and other factors. Functions depicted as being performed by separate components may in some implementations be performed by a single component, again, depending on the expected load and other needs of the system. Other configurations of servers and network topologies may work as well as those described here.

An EHR system may be configured to restrict access to patients' medical records so that only authorized users have access to them. Such restrictions may be implemented, for example, to comply with laws and/or regulations concerning the protection of confidential medical data. Access to a particular patient's chart may therefore be restricted, e.g., to a practitioner, or to the practitioner and the practitioner's office staff, or those practitioners associated together within a specific medical practice, among many possibilities.

A user may be a member of one or more health care organizations, and an embodiment of an EHR system may limit users' interaction with the EHR system so that a user may be associated with only one such organization at a time. But such an EHR system may also allow a user to switch between those organizations as needed while remaining logged in to the application. If a user belongs to more than one organization, that user may have different permissions under each and may also have access to different features of the embodiment. Depending on the EHR system, if each organization maintains a separate patient population, a user may not be able to access patients that exist within one organization while that user is logged in under a different organization.

EHR systems typically include means to authenticate the users. Well-known examples of such means include, but are not limited to, requiring a user: to log in with, e.g., a user name and password; to provide biometric information, e.g., via a fingerprint or retinal scan at the point of use; to provide a physical token or information provided by one, e.g., a temporarily valid access code; or some or all of these and/or other means. An embodiment may limit access to some or all of the functions of the embodiment, including the user interface depicted in FIG. 3 and/or other user interfaces, to successfully authenticated users or to subsets of them.

Figure 3:
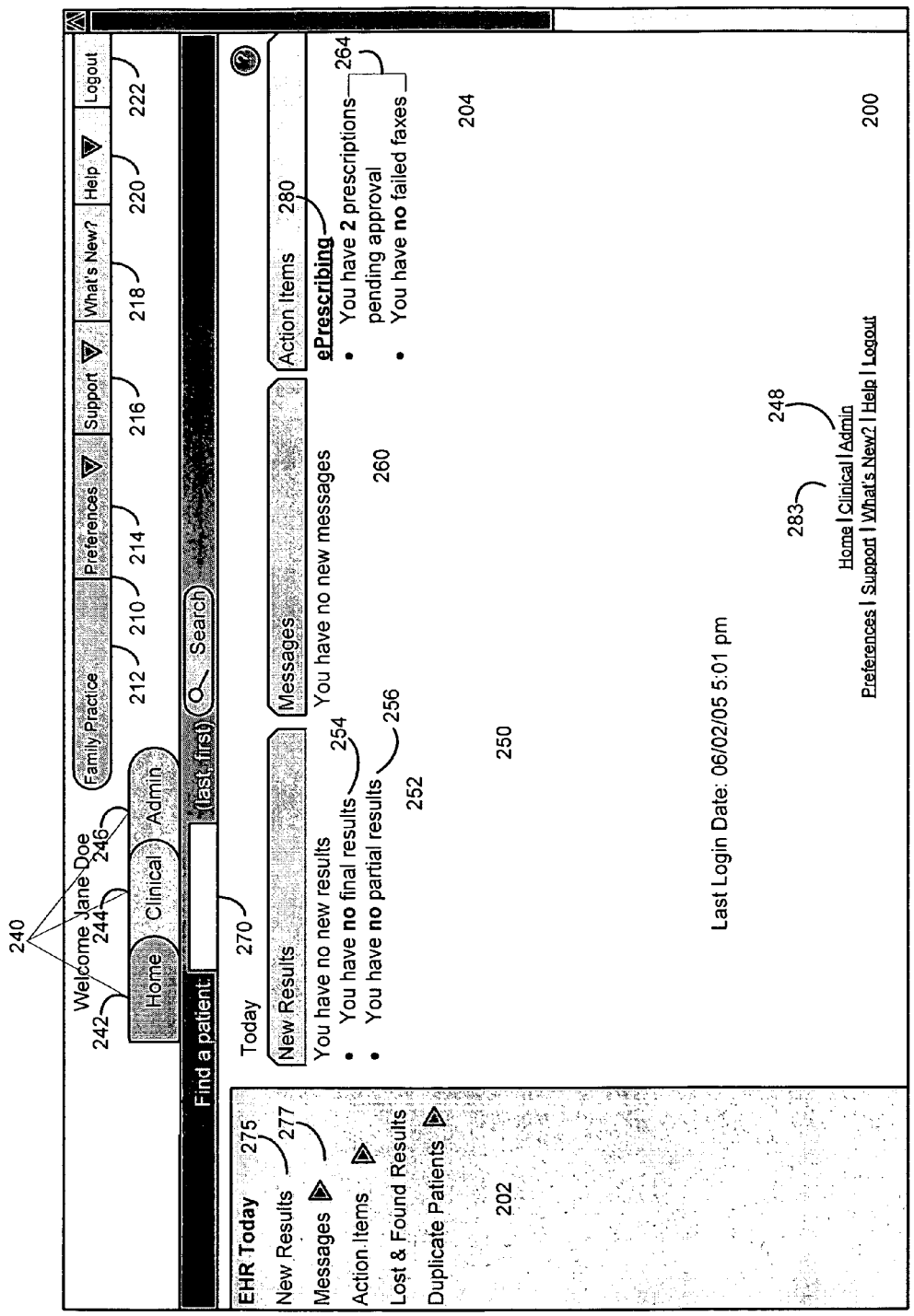
FIG. 3 depicts a user interface display adapted to navigate an embodiment of the invention.

FIG. 3 shows an initial (or "Home") screen 200 of an EHR system that may serve to allow a user to begin interacting with the system. This depicted screen 200 and those that follow may be used in connection with use of a thin client, such as a web browser. Other types of clients and/or other user interfaces (not pictured), with elements that correspond to those described herein as needed by the respective embodiments, may also be supported. EHR systems may support interaction with the user interface by well-known means for interacting with computer systems, which may comprise accepting user input via a pointing device such as a mouse and a keyboard and displaying output on a computer monitor.

The Home screen 200 may comprise certain navigation elements and cues common to some or all other user interface screens of an EHR system. Such common elements may comprise a function-specific navigation pane 202 that contains one or more links for accessing tasks related to the functional area currently being used and a function-specific content pane 204 displays content related to the task currently being performed.

Another such common element may be a navigation bar 210 that provides access to a number of general system functions. The navigation bar 210 displays the name of the organization or care site 212 currently associated with the user's interaction with the embodiment. If a user is associated with more than one organization or care site, the user may choose the one to associate with the interaction by clicking on this item.

Selecting the Preferences item 214 allows selection of one of several user preference options to see and possibly change. Such options may comprise, e.g., customizing user preference settings, specifying favorite states for pharmacy searches (discussed further below under the heading "ePrescribing"), and changing the user's login password, among other things.

Selecting the Support item 216 allows selection of one of several user support options. Such options may comprise, e.g., sending feedback to system administrators, downloading and installing available product updates, and composing an email to a support team, among other things.

Selecting the What's New? item 218 causes display of information regarding new features of the system, if any.

Selecting the Help item 220 allows selection of user documentation to be displayed. Such documentation may comprise, e.g., online help and/or a comprehensive user manual, among other things. In a particular EHR system, the selected documentation may appear in a new window (not pictured) on a computer monitor.

Selecting the Logout item 222 logs the user out of the system. In an EHR system that provides user authentication, this may have the effect of requiring a user to authenticate anew before using the other features of the system.

An EHR system's user interface may comprise functional tabs 240 that provide direct access to functional areas of the system. In the system depicted, the Home tab 242 causes redisplay of the Home screen 200, which may be updated to display the latest information available. Selecting the Clinical tab 244 provides access to patient-related services, which may comprise, e.g., patient management, lab orders, lab results, and prescription orders. Selecting the Admin tab 246 provides access to administrative functions. In typical EHR systems, not all users have permission to use administrative functions.

Some or all navigation discussed in connection with the navigation bar 210, the functional tabs 240, and/or the links displayed in the function-specific navigation pane 202 may be provided or duplicated by hyperlinks elsewhere in the screen 200. FIG. 3 shows one example of such duplication in the form of a cluster 248 of hyperlinks in the function-specific content pane 204.

The Home screen 200 may provide access to the most commonly used facilities and information provided by the system. The function-specific content pane 204 displays a snapshot 250 of many of the activities occurring within the system that relate to the user and associated patients. Such a snapshot may comprise a count 252 of the new lab results that have been received, which may be further be broken down by whether those results are final 254 or partial 256, and may also show whether any of the results are abnormal. The snapshot may comprise the number 260 of new user messages in the user's inbox, the number 264 of prescriptions that are pending approval, and/or other information.

A user interface to an EHR system may allow direct return from other user interface screens to the Home screen 200, displaying snapshot 250, through clicking on the Home tab 242. When the Home screen 200 is already displayed, clicking on the Home tab 242 may, in some systems, cause the content to be updated to the latest information available.

The Home screen 250 may provide means to navigate the information and functions provided by an EHR system. Searching for a patient, for example, may be done by entering a name in Search field 270. Upon submission of the search, the system may cause information to be displayed regarding one or more matching patients or notification that no matches were found. Such information may appear in the function-sensitive content pane of Home screen 200, or it may appear in part of another screen such as patient selection screen 290, which is discussed below in connection with FIG. 4.

Other navigational facilities may exist. The function-specific navigation pane 202 links to other facilities and information provided by an EHR system. Depending on the system and the information currently available to the user, the links may include, for example, a "New Results" link 275 that causes the system to display new lab results, if any, and a "Messages" link 277 that provides access to user messaging functionality. Other links may be present for any other information and/or facility provided by the system.

Navigational facilities may also exist within the function-specific content pane 204. For example, in the Action Items area 264, there may be links to various items that require attention. FIG. 2 depicts such a link to ePrescribing functionality, which is discussed below.

Patient Management

Use of an EHR system may be organized conceptually around one or more aspects of EHRs or their management. For example, parts of the following discussion and the accompanying figures describe EHR systems that organize access to data around individual patients and the respective records that are associated with them. (Following historical practice, a collection of records for a single patient in an EHR system is sometimes referred to as that patient's "chart.") It will be obvious to one skilled in the relevant arts that EHR systems may be organized differently, e.g., around practitioners singly or in groups, payers, hospitals, or pharmacies without affecting the substance of the systems implemented or methods performed. It will be equally obvious that EHR systems may be organized around one or more such aspects and that such organization may or may not depend on a particular user's activity at the time of use.

EHR systems typically maintain EHRs for patients. In that regard, an EHR system may provide functionality comprising some or all of adding new patients, accessing patient charts, viewing patient data, and editing patient data.

EHR systems may vary in the way they provide for access to patient data and related functionality. From screen 200 (FIG. 3), a user may select the Clinical tab 244 (or the Clinical hyperlink 283), which give access to functionality associated with clinical practice. Depending on the configuration of the system, that selection may lead directly to FIG. 4, which displays a patient selection screen 290.

Figure 4:
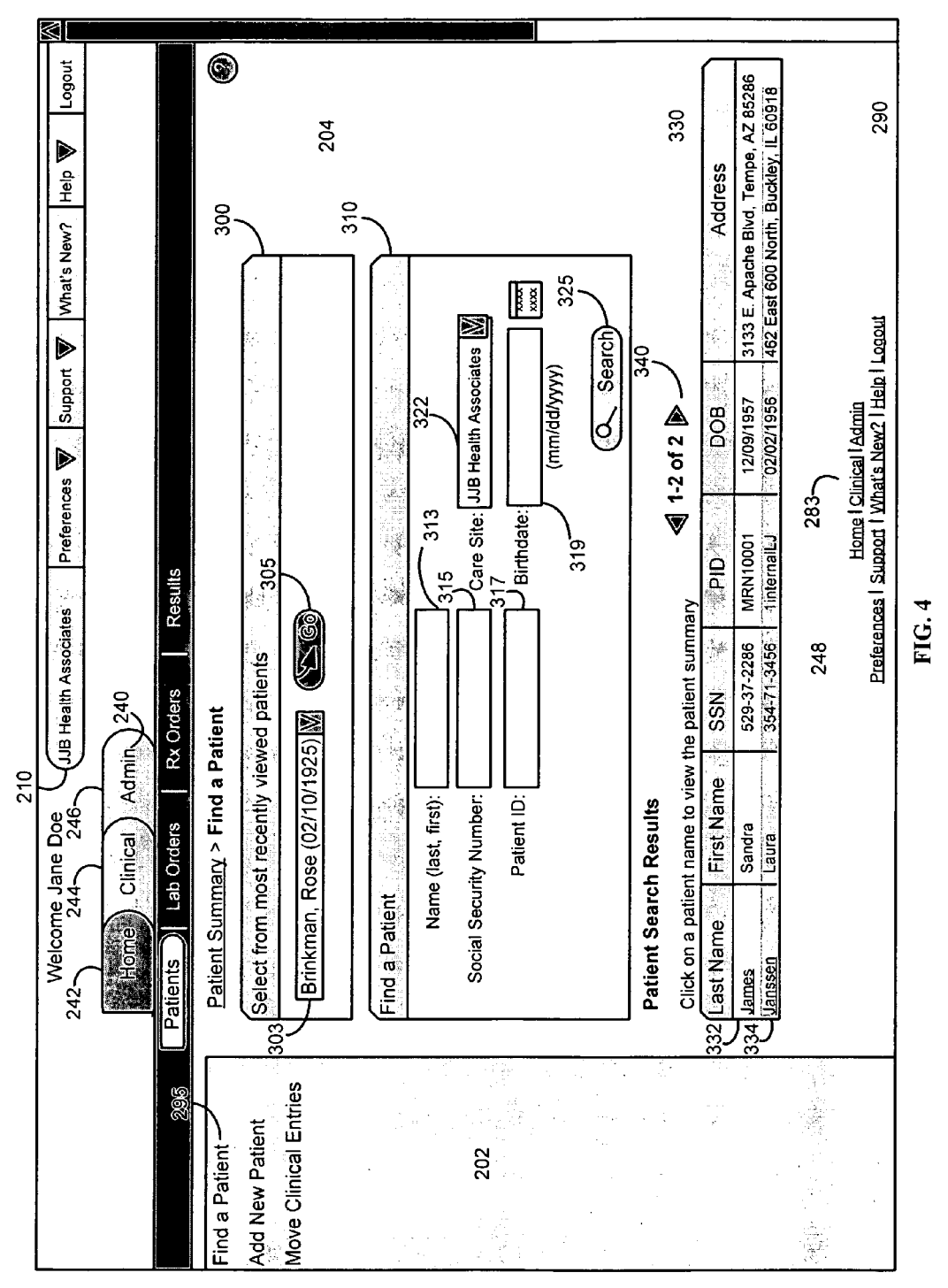

Some EHR systems may instead be configured to lead to different functionality upon selection of the Clinical tab 244 or hyperlink 283 (FIG. 3), and that functionality may then comprise links to screen 290 (FIG. 4). For example, a system may cause a link entitled "Find a Patient" 295 to appear in the function-sensitive navigation pane 202 when the Clinical tab 244 is selected. Selection of that link 295 then leads to display of screen 290.

Interfaces to one or more facilities for selecting a patient may comprise displays that appear in the function-sensitive content pane 204. One such display is an area 300 containing a drop-down list 303 of the current user's most-recently-viewed patients. (An EHR system may let an administrator set a maximum number of patients that may appear in drop-down list 303.) Once the desired patient is selected, clicking the button labeled "Go" 305 then leads to display of records associated with that patient.

Another such interface is a search area 310 containing one or more controls that support searching for one or more patients. Depending on the system, one or more of the controls may comprise text entry controls that let a user specify, e.g., a patient's name 313, Social Security number 315, patient identification number 317, and birth date 319. Some EHR systems may permit searching based on partial matches, e.g., returning all records that merely begin with the text entered by the user or allowing "wildcard" characters in one or more search criteria that can be matched by any character or string of characters.

The search area 310 may comprise other types of control. For example, a drop-down list 322 may list one or more medical practices or health care sites or facilities with which a user has relationships (collectively referred to as "care sites"). Selecting a care site from the drop-down list 322 limits the search results to patients affiliated with that care site.

An EHR system may allow a user to execute a search after entering fewer than all possible search criteria. For example, an EHR system may support searching after the user has entered only the name "Johnson" in the Name text entry control 313. Other systems may require entry of data into some or all specific text entry controls before a search can be done.

After search criteria have been selected, the search may be executed by clicking the button labeled "Search" 325.

The search results area 330 lists patients whose records match the search criteria. Hyperlinks 332, 334 lead to display of records related to a selected patient. EHR systems may also provide means by which a user may proceed directly from the display of matching patients to one or more activities involving a selected patient, e.g., writing a prescription, ordering lab tests, or modifying a patient's medical history, among many possible options.

It may be desired to limit the number of matching patients that are displayed at once. In that case, a partial list may appear in the search results area 330, and a control 340 such as the one displayed may be provided to support moving backward and forward through the list.

Figure 5:
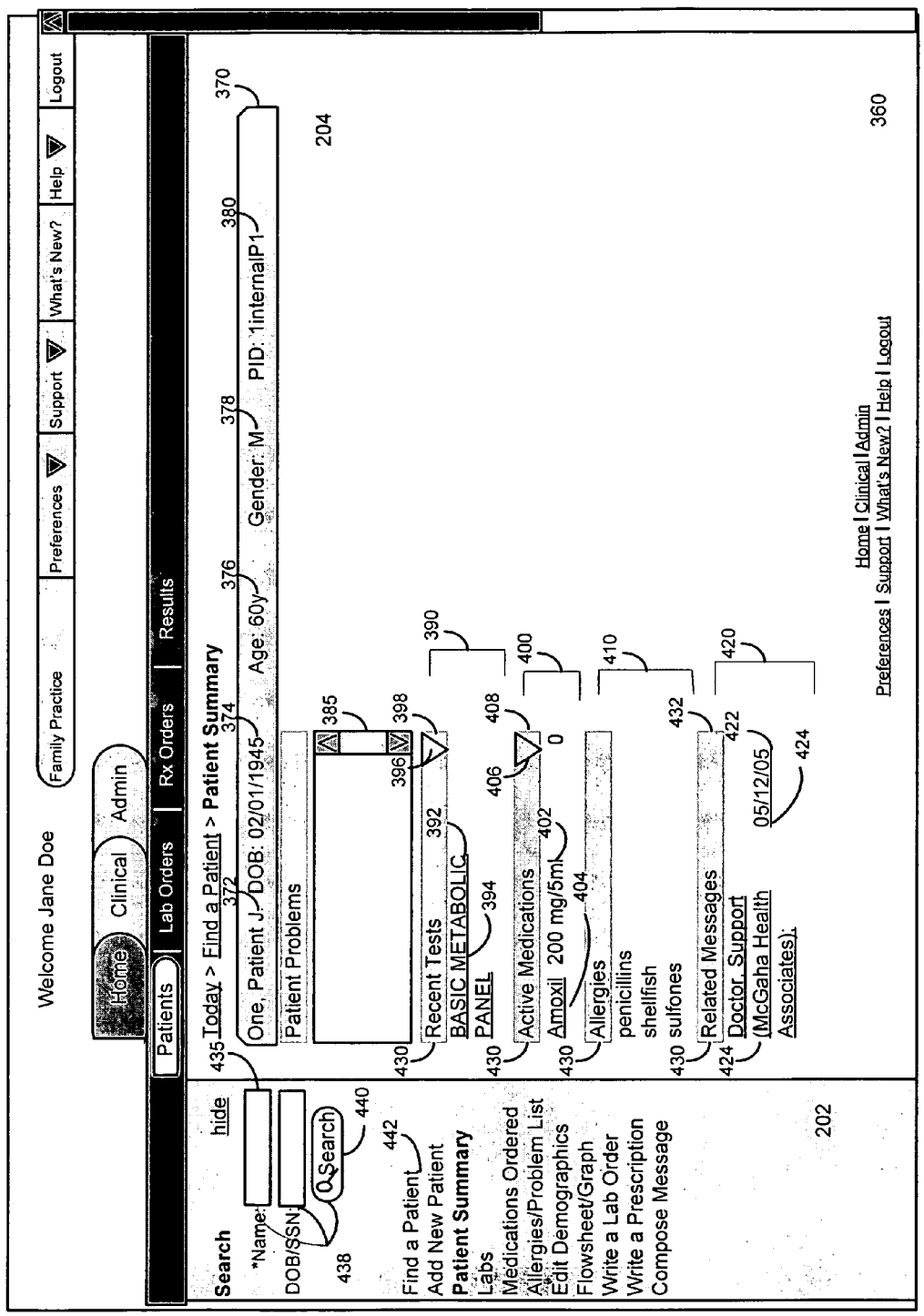
FIG. 5 depicts a user interface display that presents data associated with a patient.

In response to selection of a patient, e.g., via a hyperlink 332, 334, an EHR system may display a summary of data related to that patient, such as the summary screen 360 shown in FIG. 5. In such a system, the summary screen is a "collapsed" or summarized view of the patient's complete chart. The summary screen 360 may initially list only the latest patient data that is available for quick access and review. Viewing a more detailed history for the patient can be done by clicking individual items within each section of the summary screen 360.

The summary appears in the function-sensitive content pane 204 of the summary screen 360. The summary comprises basic information 370 that identifies the patient, including, for example, the patient's name 372, DOB (Date of Birth) 374, age 376, gender 378, and PID (Patient ID) 380.

The summary also comprises a display of patient problems and/or conditions, illustrated in FIG. 5 as an editable text area 385 labeled "Patient Problems." This text area 385 may display any problems or other notes that have been recorded for the patient. Some EHR systems allow the user to type notes directly into this control.

An area labeled "Recent Tests" 390 displays one or more lab tests 392 that have been ordered for the patient. The details of a result may be viewed by clicking on the name of the test 394.

Some EHR systems may allow viewing of tests by requisition (order). To support this functionality, the user interface screen illustrated in FIG. 5 displays a options (not shown) when the user moves the pointer over the triangle 396 in the title bar 398. For example, in response to a click on the option marked "Requisition" (not shown), tests will be presented, grouped by requisition. Other systems may support other or additional options for viewing lab tests, with appropriate user interface elements to support such options.

Lab tests are discussed in more detail below under the heading "Lab Orders and Results".

An area 400 labeled "Active Medications" displays one or more medications 402 that have been prescribed for the patient (using ePrescribing, described below under that heading) and are still active. Details may be viewed by clicking the name 404 of a medication 402 appearing in this area. The user interface screen illustrated in FIG. 5 allows viewing of all medications prescribed for the patient—including those that are currently inactive or that have been added from other sources—in response to moving the pointer over the triangle 406 in the title bar 408.

An area 410 labeled "Allergies" displays any allergies that have been recorded for the patient.

An area 420 labeled "Related Messages" displays user messages 422 that have been sent that contained a reference to the patient. As displayed in FIG. 5, a user message 422 may contain a hyperlink 424 to more information associated with the message, comprising, for example, the text of the message and some or all data attached to the message. User messages are described in more detail below under the heading "Messaging" below.

Each title bar 430 is a hyperlink or control that gives the user access to further details about the named area. For example, clicking on the "Related Messages" title bar 432 leads to more information about messages. The new information appears in the function-specific content pane 204 of user summary screen 360.

An EHR system may support searching for patients from the user summary screen 360. For example, the search entry area 435 in the function-dependent navigation pane 202 may comprise one or more controls 438 for entering partial or complete search criteria. A search may be executed by selecting the button 440 labeled "Search". An EHR system may provide a means to reach other searching facilities, such as the search screen 290 of FIG. 4, and an example of such means is the hyperlink labeled "Find a Patient" 442 in the function-specific navigation pane shown in FIG. 5.

EHR systems may also provide user interfaces (not pictured) for adding and/or deleting patients and adding, removing, and/or modifying information associated with patients. Such interfaces may use user interface components that are well known in the relevant arts.

ePrescribing

EHR systems may comprise an electronic prescribing function, referred to as "ePrescribing." ePrescribing may automate some or all aspects of prescription writing and renewal. In preparing a prescription, ePrescribing may retrieve patient benefit information from an information source such as RxHub® and its participating Pharmacy Benefit Managers (PBMs), which information may then in some embodiments be displayed to the person writing the prescription.

ePrescribing may receive prescription renewals and submit prescriptions electronically or as faxes through an electronic prescribing network such as SureScripts™. Implementations of ePrescribing may support submitting a prescription electronically to the patient's pharmacy of choice, and/or printing the prescription for hand delivery to a pharmacy. Some or all prescriptions written for a patient using ePrescribing may be stored in the patient's medication history, which may be part of the patient's chart maintained by an EHR system. The medication history can be used to store information about inactive medications as well as any additional prescription history retrieved from PBMs.

An embodiment of ePrescribing may provide various different functions that comprise some or all of: displaying information regarding insurance coverage of medications and, depending on the embodiment, possible alternatives; checking for drug-to-drug interactions per prescription, and across the patient's medication history; and drug-to-allergy interactions per prescription. ePrescribing may comprise other functions related to medications, prescriptions, insurance, and/or billing besides or in addition to those specifically named.

Figure 6:
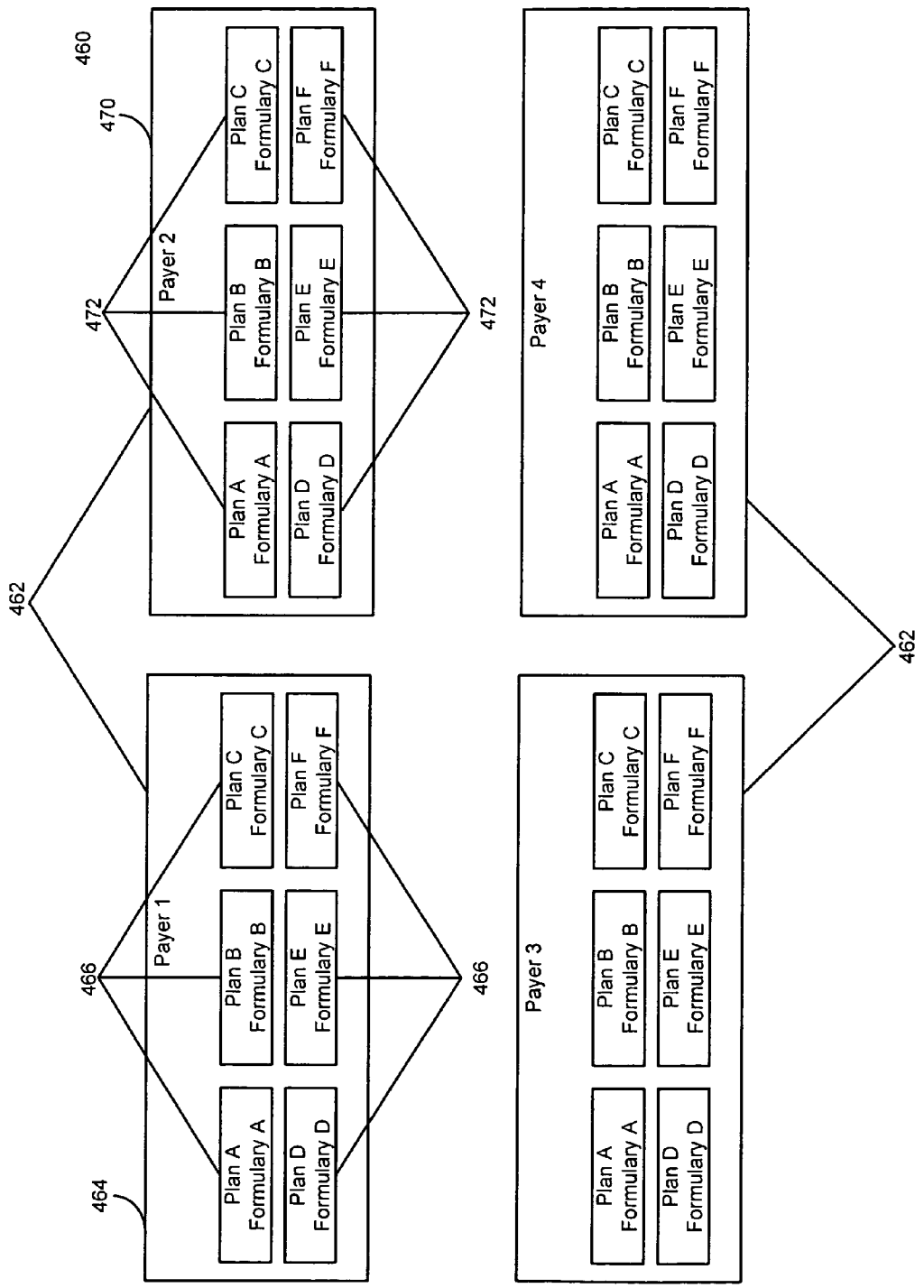
FIG. 6 schematically depicts the relationships between payers, insurance plans, and prescription drug formularies.

An embodiment of ePrescribing may comprise functions related to prescription drug formularies. A formulary is a list of drugs based on a specific payer and a specific payment plan. FIG. 6 illustrates the relationship between payers, plans, and formularies. The figure 460 shows four payers 462. Payer 1 (referenced by 464) offers six different plans 466. If, for example, Payer 1 is an employer, it may offer its employees six different plans 466, each offering different benefits and requiring a different contribution from the employee. Each of these plans 466 is associated with its own distinct formulary.

Similarly, Payer 2 (referenced by 470) offers six different plans 472, and each plan is associated with its own distinct formulary.

Embodiments of ePrescribing may maintain an Active Medications list for patients. When used to create a prescription for a patient, ePrescribing may automatically save a record of each prescribed medication to the patient's Active Medications list, which may be accessible from the patient's summary, displayed in the patient summary screen 360 (FIG. 5). Medications can also be added manually to a patient's Active Medications list by activating previously inactive medications for which ePrescribing has a record and/or by adding them from a list of prescriptions maintained by one or more PBMs.

Embodiments of ePrescribing may support user-specified rules that govern the contents of an Active Medications list. For example, a rule may set the maximum time that a prescription may be considered "active." After that time, a prescription may be removed from the patient's Active Medications list, but may or may not be retained in other records. ePrescribing may also support manual addition to and/or removal from the Active Medications list.

An embodiment of ePrescribing may provide several different ways to display information about a patient's medication history or subsets of it. For example, the Active Medications list and/or the list of all medications on the patient's chart may be displayed and may be sorted according to one or more criteria.

When displaying details of a particular medication, an embodiment of ePrescribing may permit the user to view and/or print a copy of the prescription.

Figure 7:
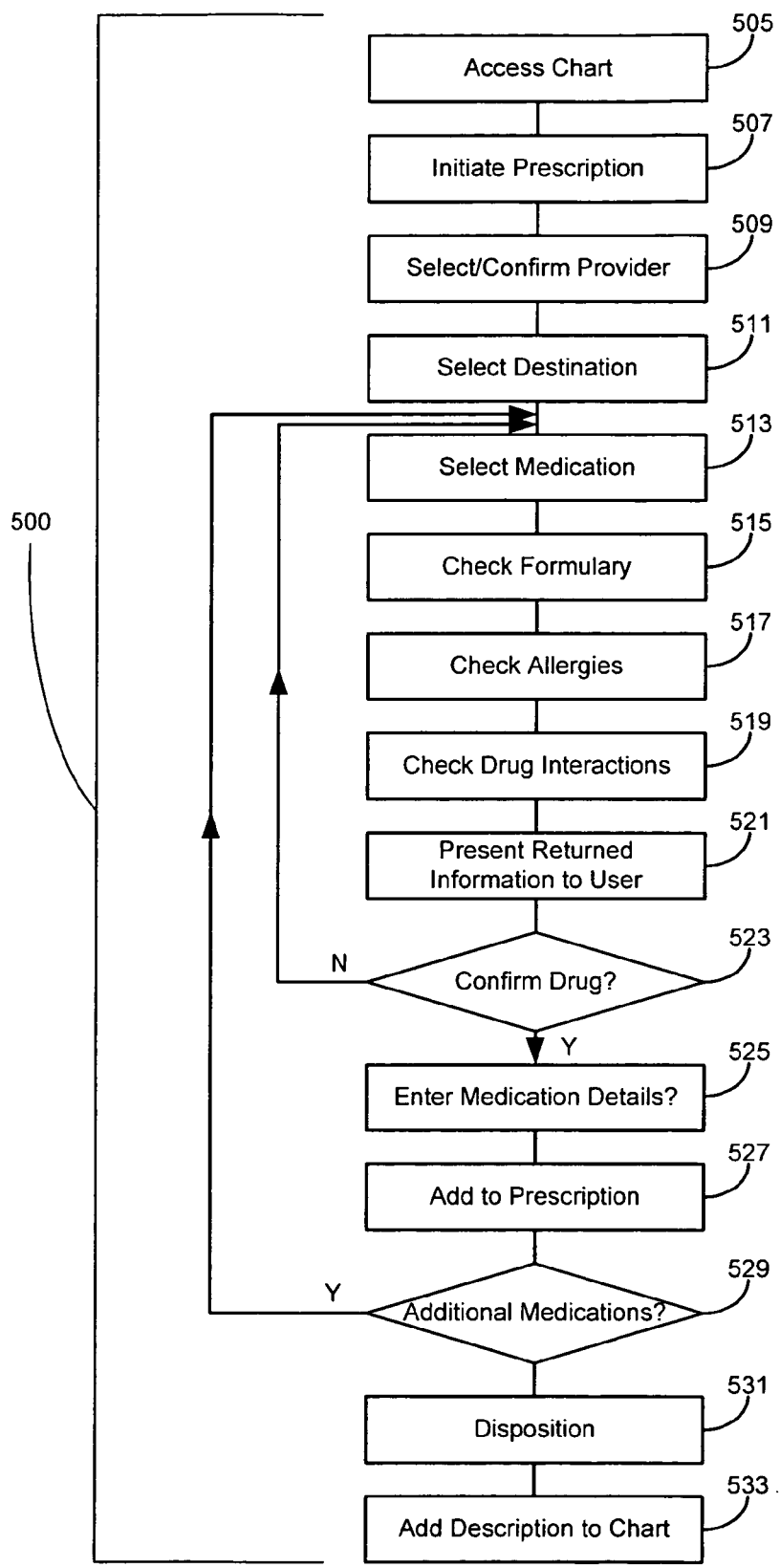
FIG. 7 depicts creation of a new prescription according to an embodiment of the invention.

FIG. 7 illustrates how a new prescription may be written 500 in association with an ePrescribing. At block 505, a patient's chart is accessed, possibly as described in connection with FIG. 4, above. Once the patient has been selected, the user may begin 507 creating the prescription.

At block 509, the identity of the health care provider who is writing the prescription is selected or confirmed. In some EHR systems, the user's login information may serve to identify a default provider, who may be the user. Some systems may permit overriding the default choice. Some may limit the choice of provider to one or more providers who have previously been associated with the user.

A destination may be assigned 511 to a prescription. Depending on the embodiment of ePrescribing, possibilities may comprise one or more of, e.g., sample or handwritten prescriptions, prescriptions sent to pharmacies electronically or by fax, and prescriptions sent electronically to mail-order prescription sellers.

Sample prescriptions may represent drugs dispensed directly by the provider, which may be samples provided to the provider by drug makers or distributors. Handwritten prescriptions may, for example, be printed by an embodiment of this application and then manually signed by the provider or manually written in their entirety by the provider. Handwritten prescriptions may be used, for example, where a pharmacy is not equipped to receive prescriptions electronically or by fax, or where applicable law or regulation requires a paper prescription bearing an authorized provider's original signature.

If the prescription is to be sent directly to a pharmacy, block 511 may comprise selection of the recipient pharmacy.

In block 513, a medication is selected for prescribing. Once the medication and the patient are selected, one or more checks may be performed against one or more databases. Depending on the embodiment of ePrescribing, such checks may comprise, for example, one or more of checking the formulary 515 applicable to the patient; checking the drug against the patient's known allergies 517; and checking for interactions 519 between drugs that the patient is known to be taking. Block 521 represents presentation to the user of the results of some or all of these checks.

After reviewing any results of any checks, the provider may confirm 523 the selected drug or to go back choose another medication 513. Once the provider confirms a selected medication, other details of the prescription may be provided 527. Depending on the embodiment of ePrescribing, such details may comprise one or more of, for example, the dosing frequency, the amount of the medication to be dispensed, the length of time that the patient ought to take the drug, the number of refills allowed, and whether a brand-name drug, if prescribed, may be replaced by its generic equivalent, if any.

An embodiment of ePrescribing may support prescriptions that comprise one or more medications. In such embodiments, block 529 represents the choice to add a medication to the prescription that is in progress.

Following selection of desired medications, block 531 represents disposition of the prescription. Depending on the embodiment of ePrescribing and/or the options associated with the prescription, possible dispositions may comprise, for example, printing a prescription for manual signature, transmitting the prescription to a pharmacy electronically or by fax, and/or storing the prescription for possible future action, possibly comprising, among other things, electronic review by a payer. Block 533 represents addition of a prescription to a patient's chart.

Embodiments of ePrescribing may support the association (not pictured) of notes with a prescription and/or some or all of the medications contained in it.

Figure 8:
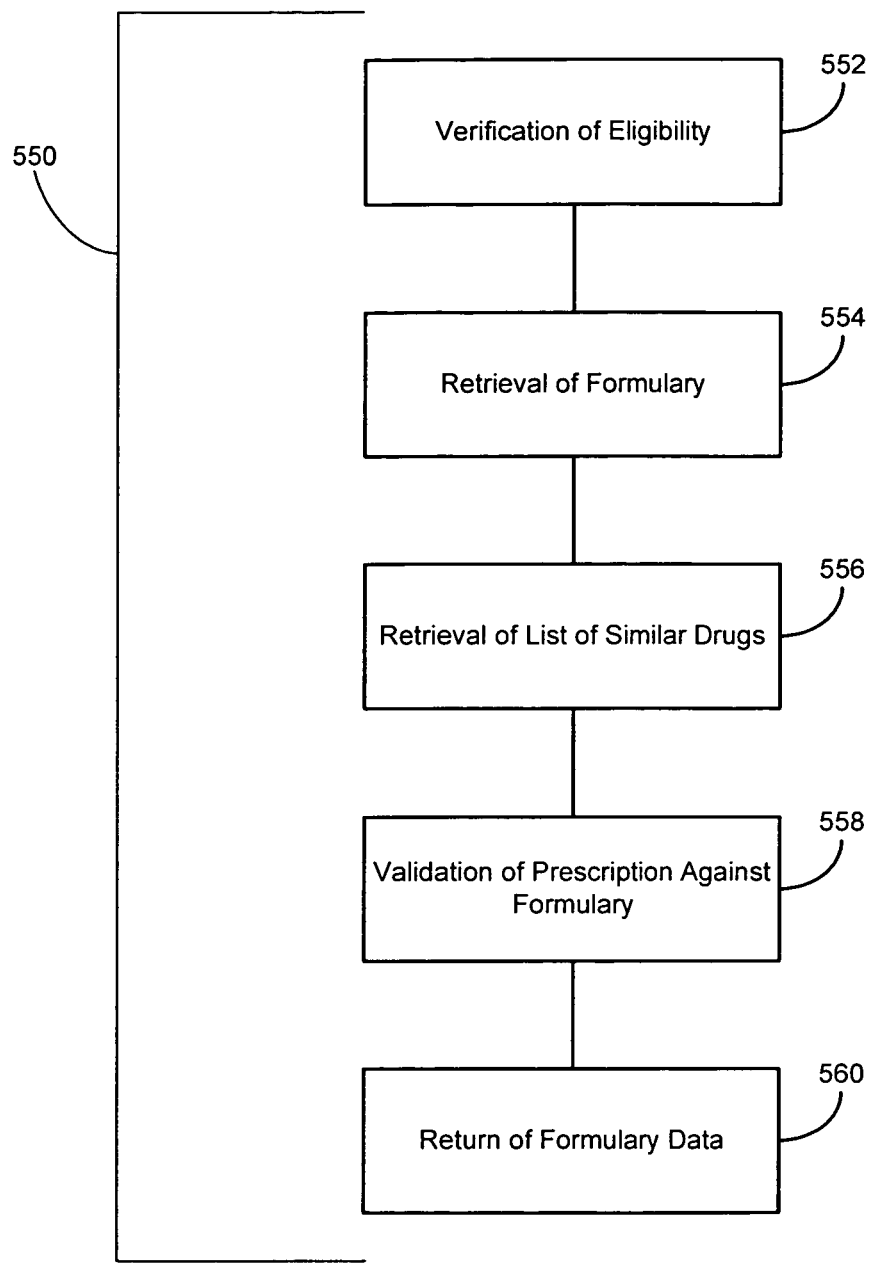
FIG. 8 depicts checking a medication against a particular prescription drug formulary.

FIG. 8 elaborates a possible implementation 550 of checking a formulary. Formularies exist because formulary management may benefit payer organizations. The payers make available the different formulary options to meet both the financial needs of an employer and the benefit needs of employees. But since there are thousands of payers and each payer can have several plans, there are thousands of plans and formularies, all of which may need to be managed.

In block 552, the patient's eligibility for a particular plan is checked against one or more databases. If the patient is eligible, then the appropriate formulary for that plan is retrieved in block 554.

From one or more databases, from the formulary, or both, a list of drugs similar to the prescribed drug is retrieved in block 556. A "similar" drug here is a drug with some or all of the same indications as the prescribed drug, or a drug that is prescribed in similar circumstances.

In block 558, the validity of the prescription is checked against the formulary. Finally, in block 560, the results of the other blocks are returned. In some implementations of ePrescribing, the provider will be told that the prescribed drug is or is not on the formulary and will also be shown the list of the similar drugs that were identified in block 556. If the information is available to the electronic prescribing system, the provider may also be told what co-payment will be required for the drug.

Other ways (not pictured) exist to check formularies. For example, all relevant formulary data may be obtained at the commencement of an ePrescribing operation. Then, before any information regarding a drug is presented, that drug is checked against the applicable formulary, and the displayed information reflects he formulary status of the drug.

Figure 9:
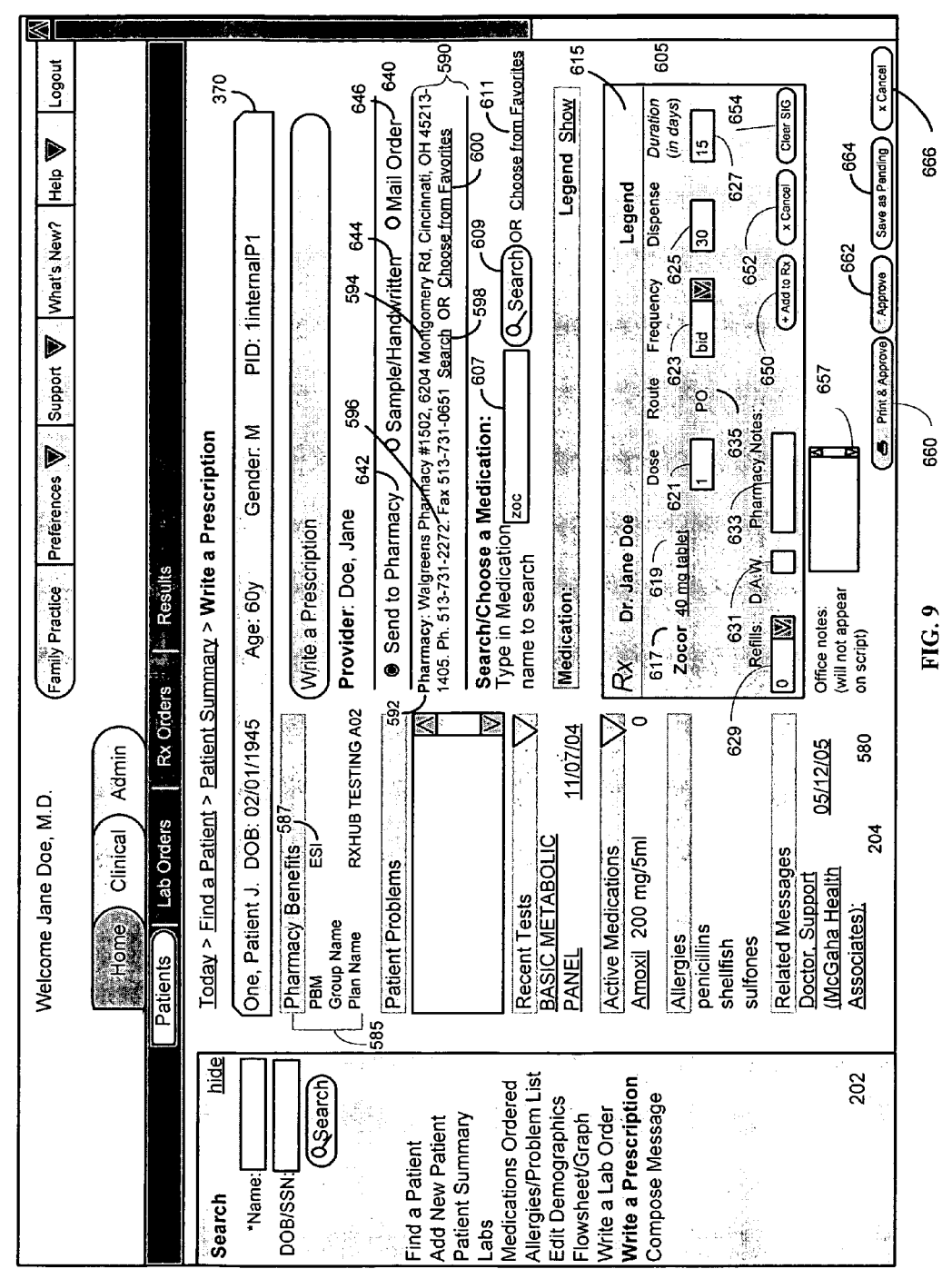

FIG. 9 depicts an example of prescription writing screen 580 that may be used in association with embodiments of ePrescribing.

As in other example screens, the prescription-writing screen 580 displays basic information 370 that identifies the selected patient. An area 585 holds information about the patient's pharmacy benefits, if known. The information comprises the name of the PBM 587 from which formulary information will be retrieved, if available.

A pharmacy display area 590 holds information about the currently selected pharmacy, which may comprise, for example, the name 592, location 594, and telephone number 596. An embodiment of ePrescribing may set a default pharmacy that may be accepted or modified. A user may select a new pharmacy by following a hyperlink 598, to a screen (not pictured) from which the user may search for a pharmacy, or by following a hyperlink 600 to a display (not pictured) of one or more "favorite" pharmacies, the contents of which depend on the embodiment.

An embodiment of ePrescribing may allow the user to add pharmacies manually (not pictured). Depending on the embodiment, an administrator may allow only a subset of users to add pharmacies manually. Some embodiments may support limiting use of such manually-added pharmacies to one or more subsets of users, and such individual limitations may or may not apply to individual pharmacies and/or one or more classes of pharmacies.

A medication selection area 605 supports searching for a medication to add to the prescription. After a partial or full name of a medication is entered into the text entry control 607, clicking the button labeled "Search" 609 executes a search. From the results of such a search (not pictured), the user may select a medication to prescribe. Embodiments of ePrescribing may also support conducting further searches or other means of selecting a medication once a search has been performed. Also in the medication selection area 605 is a hyperlink 611 that leads to a display (not pictured) of one or more "favorite" medications, the contents of which depend on the embodiment. Selection of a medication may cause display (not pictured) of one or more forms and/or dosages in which that medication may be dispensed.

Any display of information related to a medication may comprise information regarding the formulary status of that medication. Many ways of conveying such information are well-known, and may comprise, e.g., arranging names of medications in a display; providing textual labels; visually associating one or more icons with the displayed medication; and/or varying the typeface, size, style, color and/or other attributes of the text used; among other indications.

In addition to or instead of the preceding, any display of information related to a medication may comprise information regarding interactions between that medication and a patient's allergies and/or other medications that a patient is known to be taking. Display of such information may take varying forms as above.

Display of information related to a medication may comprise display of information regarding other medications, comprising, for example, generic equivalents to a medication and/or possible alternatives to a medication.

The Rx Box 615 displays a selected medication 617 and its dosage and form 619. It contains controls that support entry or modification of information associated with a prescription, such as the dose 621, frequency 623, amount to be dispensed 625, duration of the prescription 627, number of refills permitted 629, authorization to dispense a generic equivalent instead of a brand-name drug 631, and notes 633, if any, for the pharmacy. A code 635 indicates the preferred route for administration of the medication. Some embodiments of ePrescribing may cause additional and/or different controls to be displayed.

As illustrated, the dose 619 is a hyperlink to a screen (not pictured) allowing selection of a different dose, if available.

A destination area indicates where a complete prescription is to be sent. As depicted, the options presented comprise "Send to Pharmacy" 642, "Sample/Handwritten" 644, and "Mail Order" 646. Options may be disabled depending on circumstances. For example, when used to create a prescription for a controlled substance that may be dispensed only upon a manually signed prescription, an embodiment of ePrescribing may disable the "Send to Pharmacy" 642, and "Mail Order" 646 options.

Once a medication has been selected and appropriate parameters set, a button 650 allows addition of the medication to the current prescription. Another button 652 causes removal of the medication from the current prescription. A button 654 is provided to clear the currently-entered values.

Embodiments of ePrescribing may provide functionality and interfaces (not pictured) supporting renewal of previous prescriptions and/or for using previous prescriptions as models or templates for new ones.

Screen 580 also displays a control 657 that supports entry of office notes that are associated with the prescription as a whole, but may or may not be associated with any individual medication contained in the prescription. Depending on the embodiment of ePrescribing, such office notes may or may not appear on a prescription itself.

Screen 580 displays controls 660, 662, 664, 666 associated with the disposition of prescriptions. Depending on the embodiment of ePrescribing, a button 660 causes a prescription to be printed, an image of a prescription to be displayed that may itself be printed, or both. A button 662 indicates approval of the prescription as currently displayed. Selecting this button 662 may cause the prescription to be sent to the selected pharmacy, to be held pending approval by a PBM, and/or other possible dispositions. A button 664 causes the prescription to be saved as a pending prescription, and, in some embodiments, the prescription may be held pending approval by a PBM. Finally, a button 666 may cancel a prescription.

Information about pending and sent prescriptions may appear on screen 200 (FIG. 3) in the Action Items area 264 (FIG. 3). Such information may comprise, for example, the number of pending prescriptions and/or the number of electronic or faxed prescriptions that failed to reach their destinations. In some embodiments of ePrescribing, a hyperlink such as the hyperlink 280 (FIG. 3) illustrated may lead to a display (not pictured) adapted to resolution of one or more such action items.

The preceding description of ePrescribing is meant to be illustrative, not limiting. Embodiments of ePrescribing may provide functionality and user interfaces different from and/or in addition to those described. Tools may be provided to search, retrieve, display, modify, and/or otherwise manipulate data associated with prescriptions and/or associated medications, whether singly, in groups, or both.

Lab Orders and Results

EHR systems may support entry of orders for lab services and/or display of results of lab tests. More particularly, a user interface may support specification of one or more lab tests to be performed and, depending on the system, may automatically submit a request for such tests to a provider of lab services (a "lab"). Automatic submission of a request may take place electronically, by fax, and/or by other means. Labs may provide test results for storage, processing, and/or display. An EHR system may insert some or all lab orders and/or results into the involved patient's chart.

EHR systems may support entry of orders for lab services and/or display of results of lab tests.

Figure 10:
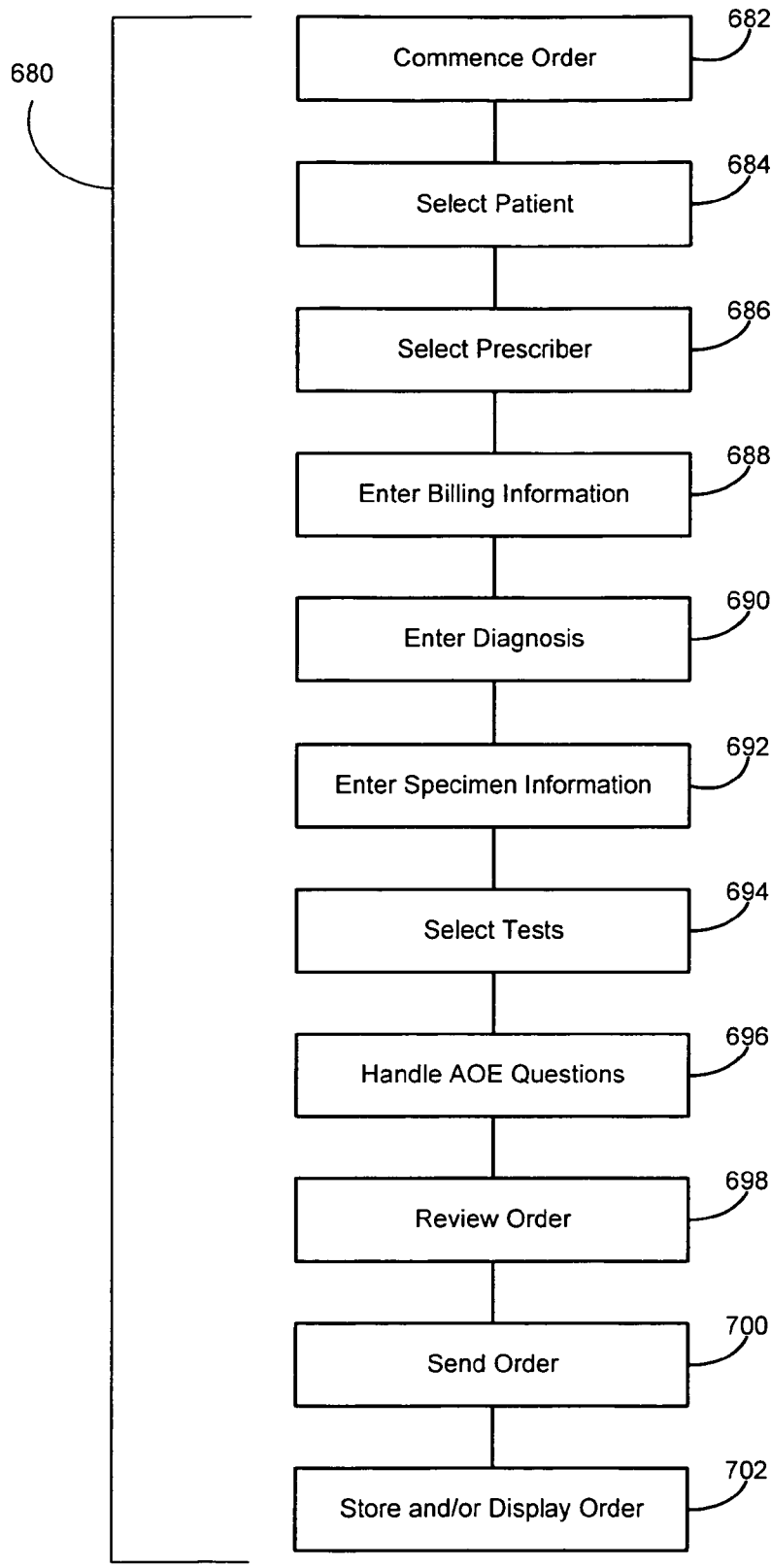
FIG. 10 depicts ordering laboratory services according to an embodiment of the invention.

FIG. 10 depicts how a new order (also called a "requisition") may be created 680. In block 682, a user interface adapted to creation of an order is displayed. In block 684, a patient is associated with this order. If order creation 680 has been initiated from a screen such as patient summary screen 200 (FIG. 3), a patient may already be associated with this order. An EHR system may provide functionality as already described herein to select a patient to associate with this order.

Block 686 represents selection of the health care provider who is ordering the test. EHR systems may support use of one or more unique codes and/or identifiers in connection with selection of a provider. For example, an EHR system may restrict the ability to order lab tests to physicians, and such a system may support use of the ordering physician's Medicare Unique Physician Identification Number ("UPIN") to uniquely identify that physician.

An EHR system may support entry 688 of billing information for the associated patient and/or verification of such information already provided. Such information may comprise, for example, the name of the person who bears financial responsibility for the patient and/or information regarding the patient's insurance or other payment arrangements. An EHR system may use this information in conjunction with one or more facilities for automating payment, billing, and/or collection.

In block 690, one or more diagnoses associated with the patient may be entered. Diagnoses may be represented by one or more codes, e.g., codes from the standard International Classification of Disease (ICD). An EHR system may accept locally-defined codes in addition to or instead of standard codes. Similarly, an EHR system may accept textual specifications of diagnoses in addition to or instead of codes of any sort.

One or more specimens may be subjects of lab tests. Block 692 represents entry of information regarding a specimen associated with a test order. Such information may comprise, for example, the date and time the specimen was collected, the volume of the specimen, and/or whether the patient fasted. An EHR system may vary the information collected depending on which test is selected and/or may refuse to accept an order that omits some or all information.

In block 694, depending on the system, one or more lab tests may be selected. Also depending on the system, a user may select from tests offered by one lab or from a plurality of labs.

An EHR system may provide access to one or more tests that require additional information before a lab can perform the tests. In block 696, such Ask at Order Entry ("AOE") information can be obtained and added to the order information.

An EHR system may use entered patient, payment, diagnosis, order, and/or AOE information to verify (not pictured) that a test order will be covered by the patient's payment plan. Such a system may indicate coverage status visually.

Block 698 depicts review of entered order information. In some EHR systems, creation 680 of a lab order may be interrupted (not pictured) at this point, with the order information stored for future use. In such a system, such stored information may be retrieved and the order completed. Once the information is believed correct, the order may be sent in block 700 to, depending on the embodiment, one or more labs for processing. In block 702, a sent order may be stored, possibly in association with the patient's chart.

Sending an order as depicted in block 700 may comprise sending the order to a lab electronically, by fax, and/or other means, depending on the EHR system and/or its configuration.

Following creation 680 of a lab order as depicted in FIG. 10, an EHR system may arrange automatically for retrieval (not pictured) of the physical specimen or specimens associated with one or more ordered tests. Such arrangements may comprise, for example, adding the location of the health care provider's office to the route of a courier who picks up such specimens. In some EHR systems, an order may request that a technician be dispatched to the patient's location (e.g., home or office) to obtain a sample. Another possible arrangement may involve automatic generation of shipping orders and documents for a common carrier such as UPS® or FedEx®. It will be appreciated that many other such arrangements are possible.

An EHR system may support variations of lab order creation 680 in addition to or instead of creation 680 as depicted. For example, information entered as described may serve to create a standing lab order, which may be repeated as specified by the user. A previously-entered order may serve as a template for creation of a new order. Many other variations are possible and may be supported by an EHR system.

Test results may be provided electronically to an EHR system. An EHR system may accept result in other forms, e.g., results printed on paper may be accepted via optical scanning or manual data entry. Other ways to provide and accept test results are apparent. An EHR system may accept test results regardless of whether a test was electronically ordered.

An EHR system may receive one or more test results that lack information sufficient to match the results with a requisition or a patient. A system may thus provide one or more facilities for matching such orders with the corresponding records.

Figure 11:
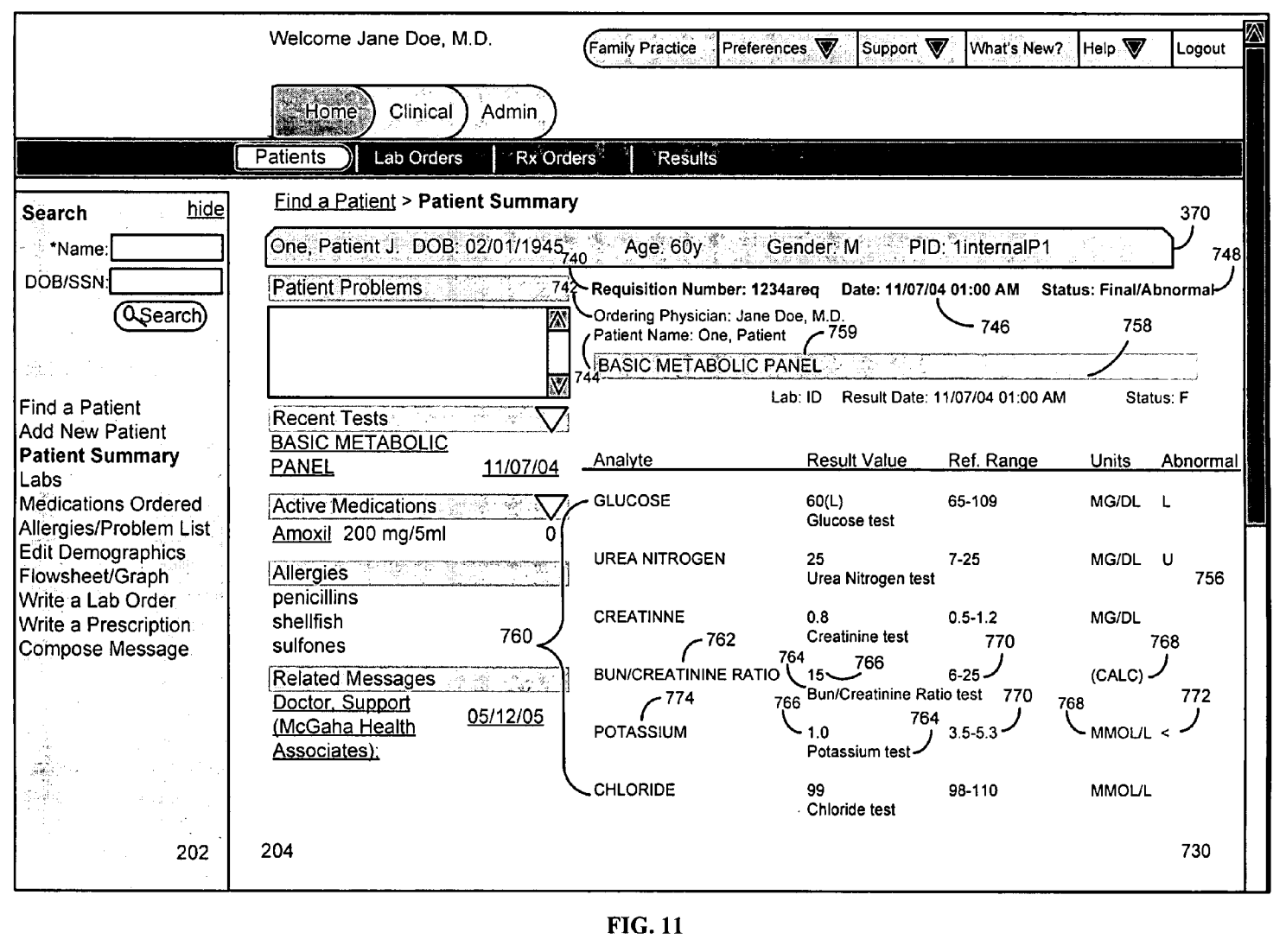

FIG. 11 depicts the test result screen 730 that may appear in an EHR system. An EHR system may provide one or more ways to reach test results, and one way that the depicted screen 730 may be reached is from the patient summary screen 360 (FIG. 5). The test result screen 730 comprises basic information 370 that may identify the patient associated with a test. The test result screen 730 may comprise other information about the test results and the associated requisition, e.g., a requisition number 740, the prescriber's name 742, the patient's name 744, the date and/or time when the tested sample was obtained 746, and/or a summary 748 of the test results, among other things.

Test details 756 may be presented. A title bar 758 indicates the name 759 of the test and/or panel of tests. Below the title are the results 760 of one or more tests.

As illustrated in the test result screen 730, a test result 760 comprises the name 762 of a substance or property (either may be called an "analyte") for which a test was performed. The result 760 may also comprise a short description 764 of the test or analyte; a number representing the value 766 of the analyte; and/or the units 768 of the measurement. For reference, a range 770 of typical values for the analyte may be provided, as well as one or more visual indications 772 that a measured value is abnormal.

For example, the test result screen 730 illustrates the results of a panel of tests called a "Basic Metabolic Panel." One test in the panel is a test for potassium 774. The reference range 770 for potassium is between 3.5-5.3 millimoles per liter, but the test measured only 1.0 millimoles per liter 766. A "<" character 772 thus appears to the right of this abnormal result, indicating that measurement was below a range that may be considered normal. A user interface screen may comprise other indicia of abnormal test results, e.g., symbolic icons and/or text coloring.

Test results over time may be presented. For example, graphs and/or charts (not pictured) may depict the values of one or more tests over time. A report may present the same information textually. Other ways of presenting test results will be apparent, and an EHR system may comprise any or all such presentations.

An EHR system may comprise search, retrieval, and/or report generation facilities (not pictured). Such facilities may, depending on the system, comprise manipulation of one or more test results for one or more patients, individually or collectively. For example, an EHR system may allow a user to search for results of all glucose tests given in the past month to male patients between the ages of 45 and 59, in which the test detected an abnormal level of glucose. Such facilities may serve, for example, to identify clusters of abnormal test results, which may in some circumstances signal a spreading health problem. An EHR system may comprise tools for creating graphical and/or textual reports of such searches.

User Messaging

An EHR system may comprise an electronic messaging facility that embodies this invention. According to such an embodiment of the invention, users can communicate with other users whether they reside in the same organization or care site, reside in a separate physical office location, or are members of a separate organization. An embodiment of the invention may make it possible to refer, within the user message, to specific clinical acts for a patient, including, for example, lab reports, medications, and/or allergies. This function may be desirable for purposes related to patient care, including, for example: patient referrals; answering of patient questions; and providing care instructions to other clinicians.

Figure 12:
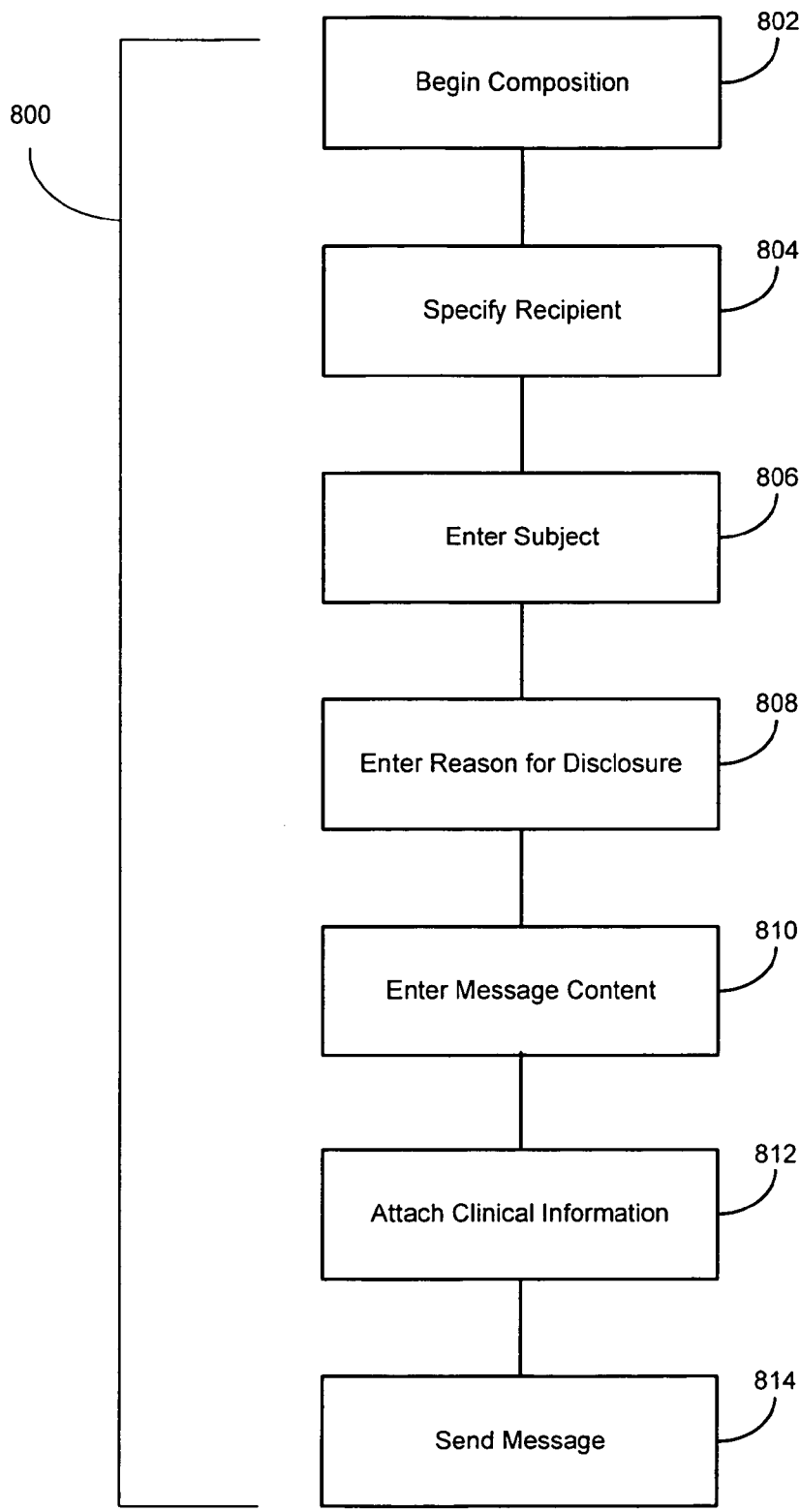
FIG. 12 depicts composing and sending an electronic message according to an embodiment of the invention.

FIG. 12 depicts composing and sending 800 a message in accordance with an embodiment of the invention. An EHR system may support one or more means to begin 802 composing a message. For example, in the patient summary screen 360 (FIG. 5), the function-dependent navigation pane 202 (FIG. 5) may contain a hyperlink 446 (FIG. 5) to a user interface that supports composing a message.

In block 804, the user may specify one or more message recipient(s). EHR systems may differ on how recipients are specified. For example, an embodiment provide a control (not pictured) in which a name or address of a recipient may be entered. An EHR system may provide the names of one or more known users, from whom one or more recipients may be selected. These and other ways of selecting recipients are well known in connection with electronic messaging, and EHR systems may support one or more such ways.

Other information may be entered; for example, an embodiment of the invention may support entry of a message subject 806, a reason for disclosure of patient information 808, and/or the content of the message 810. An embodiment may, for example, support entry of a reason for disclosure of information to track the distribution of health information that is required by law to be kept confidential.

If desired, clinical information from a client's chart may be attached 812 to the user message. The user message may then be sent 814.

Figure 13:
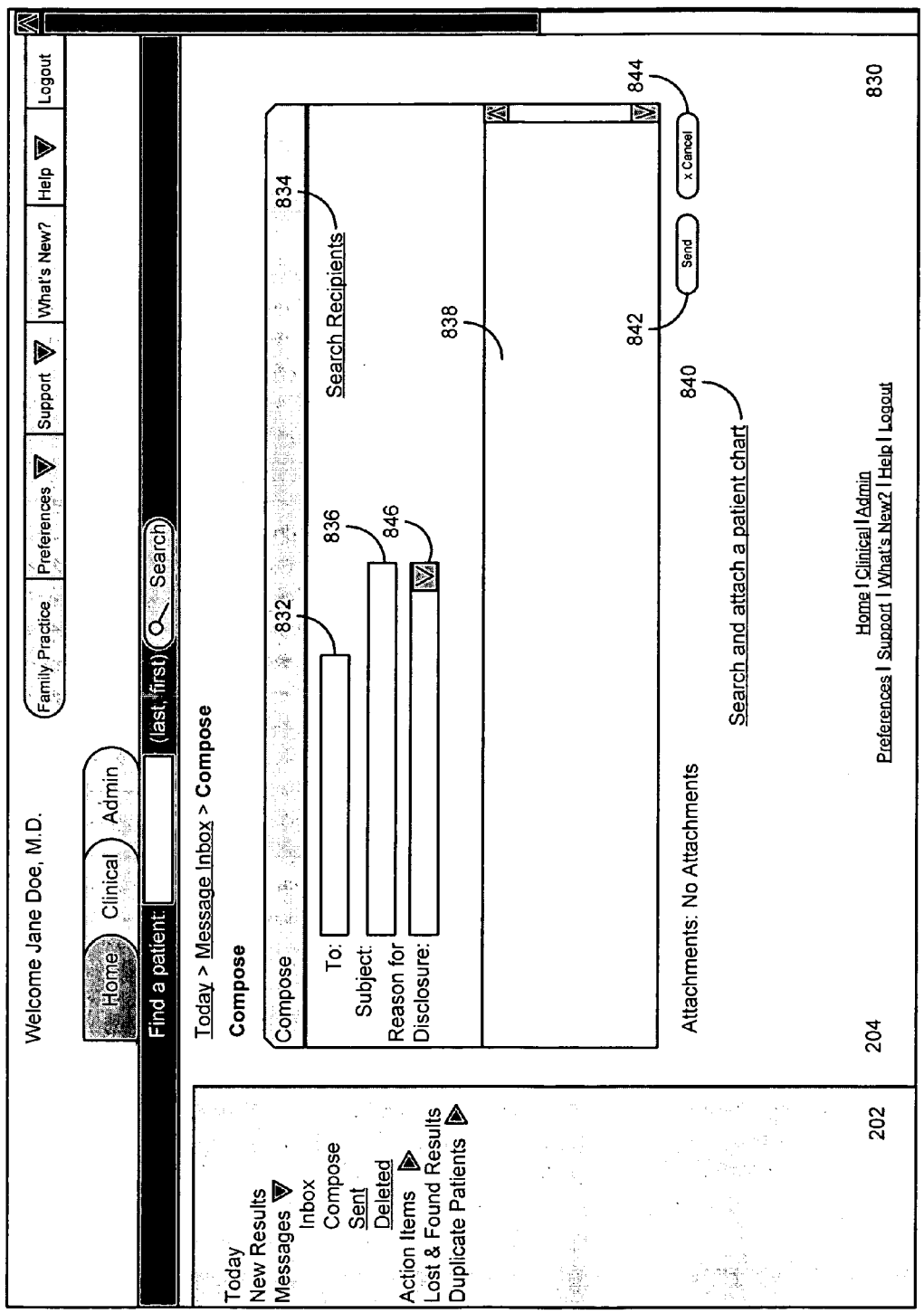
FIG. 13 depicts a user interface display suitable for composing and sending an electronic message according to an embodiment of the invention.

The message composition screen 830 of FIG. 13 depicts a user interface display adapted to composing and sending a user message. A text box 832 contains the names of one or more recipients. Depending on the embodiment of the invention, recipients' names may or may not be directly entered in text box 832.

Recipients may also be entered by following the hyperlink 834 labeled "Search Recipients." The hyperlink 834 may lead to a display (not pictured) allowing entry of one or more criteria to be used to search for potential recipients of the message. The hyperlink 834 may lead also, depending on the embodiment, to a display (not pictured) of the names of one or more recent recipients of user messages. Depending on the embodiment of the invention, one or more recipients may be added though either means or both. Embodiments of the invention may provide other ways to add recipients in addition to or instead of the ones described here.

Text areas support entry of a subject 836 for the message and the message body 838.

The hyperlink 840 labeled "Search and attach a patient chart" may serve to attach chart data to a message. When followed, the hyperlink 840 may lead to a user interface that supports selecting a patient, such as, for example, the patient selection screen 290 depicted in FIG. 4. In some embodiments, if message composition was initiated from a screen associated with a patient, such as, e.g., the patient summary screen 360 depicted in FIG. 5, searching for and/or selecting a user may be skipped.

Depending on the embodiment of the invention, once a patient has been selected, a screen such as the patient summary screen 360 (FIG. 5) may be displayed. That screen, in turn, may be used to access that patient's chart data. Individual items of data may be selected. Once desired items have been selected, a hyperlink (not pictured) or other means may enable return to the message composition screen 830. Upon return to the message composition screen 830, the selected data items will have been attached to the message. Embodiments of the invention may support removal of attached data from a draft message and/or attachment of further data.

The button 842 labeled "Send" allows sending the message, including any attachments. The button 844 labeled "Cancel" allows cancellation of a pending message. An embodiment of the invention may also provide means (not pictured) by which a draft of a message may be saved and then sent later, possibly after further revision.

In an embodiment of the invention, the message composition screen 830 may comprise a control 846 for entry of one or more reasons for disclosure of patient information. Such reasons may be legally required or otherwise desirable.

FIG. 14 is a partial representation of an electronic message 862 with attached chart data according to an embodiment of the invention. The representation uses the eXtensible Markup Language (XML), which is a well-known tool for representing structured data for storage, processing, and/or transfer.

The representation of the message 862 comprises three top-level components. The first top-level component is the header 864, which, depending on the embodiment of the invention, may comprise information relevant to handling the message, e.g., the sender 866, the recipient 868, and/or the subject 870 of the message, among other things.

The second top-level component is the body 874, which in this illustration contains only the text of the message.

The third top-level component is the attachment element 880, which may comprise zero or more attachments 882. The illustrated representation does not directly represent attached chart data, but instead contains a reference 884 (often called a "pointer") that uniquely refers to a specific entry on a specific patient's chart. The meaning and resolution of references depends on the embodiment. One possible meaning (of many) is that the reference 884 is a unique identifier that is part of the record of the chart item that appears in one or more tables in a relational database management system. The existence of a unique identifier called a "primary key" is well known in the relevant arts, and some embodiments may use a representation of a primary key as a reference 884 to chart data.

The XML fragment of FIG. 14 serves primarily to illustrate the data that a message may in some embodiments comprise, by depicting certain aspects of data associated with a message and one possible representation of those aspects. It will be appreciated that different and/or additional data may be associated with a message and that many other representations are possible, including, for example, differently-structured XML documents and/or representations other than those using a markup language such as XML. For example, an embodiment of the invention may store data associated with a message in one or more fields of one or more tables in a relational database management system.

An embodiment of the invention may use the reference 884 to identify the item of chart data referred to. This process may be called "dereferencing." Dereferencing a pointer reveals an item of chart data, which the recipient may view. If the item is saved to a patient's chart, an embodiment of the invention may duplicate the item and then save the new copy in association with the recipient's version of that patient's chart. Instead of duplicating an item of chart data, an embodiment of the invention may give the recipient direct access to the item on the sender's chart.

Some embodiments of the invention may support both options, choosing one or the other based on circumstances. For example, if the sender and recipient are in practice together, they may have access to the same charts. In that case, viewing an attached item of chart data may comprise accessing the shared chart. If the sender and receiver are not in practice together, the recipient may lack privileges to access the sender's chart directly, and the attached chart item may then be duplicated, and the copy saved, as already described.

Figure 15:
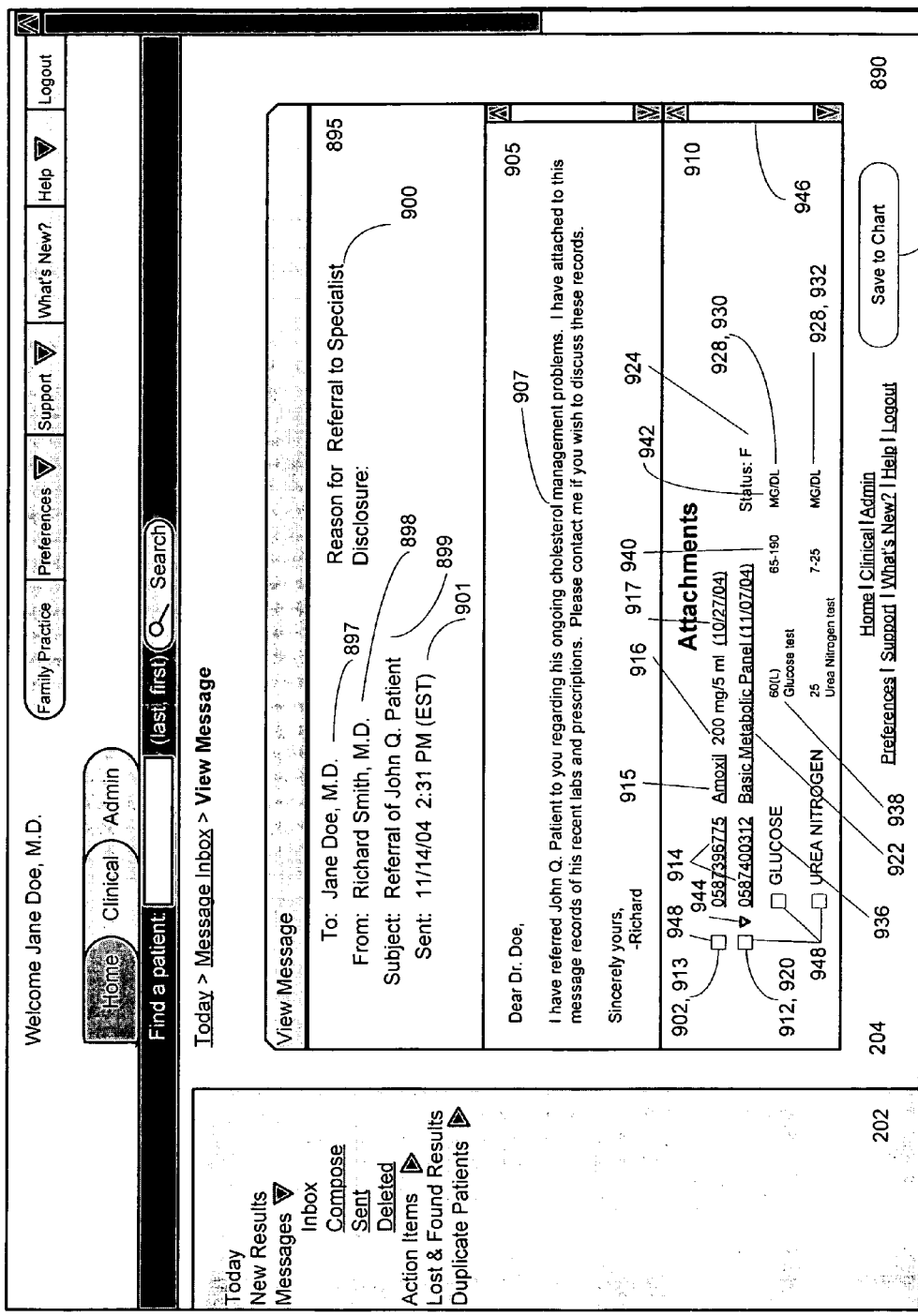
FIG. 15 depicts a user interface display suitable for viewing an electronic message and saving a persistent copy of data attached thereto according to an embodiment of the invention.

After an electronic message has been delivered, it may be viewed, and, in some embodiments of the invention, some or all attached data may be viewed and/or saved to a patient's chart. FIG. 15 depicts a user interface display 890 that an embodiment of the invention may use to present a message and attached data and to allow the recipient to view attached chart data and possibly to save it.

The message display may be divided into three areas. A header area 895 may display information about the message itself. In an embodiment of this invention, this information may comprise, e.g., the recipient 897 and sender 898; a subject, title, or summary of the message 899; the reason 900 for disclosing the attached patient records (if any) to the recipient; and the time 901 when the message was sent. The header area 895 may display other information in addition or instead of the depicted information.

A body area 905 displays the body 907 of the electronic message. In an embodiment of the invention, the body 907 comprises text. In other embodiments of the invention, the body 907 may comprise images and/or other multimedia content (not pictured) and/or hyperlinks to other data (not pictured).

An attachments area 910 displays information associated with attachments 912, if any, to the electronic message. In the depicted embodiment of the invention, each line comprises a summary of information about a single attached chart item. For example, the first displayed chart item is a prescription 913. The display is a summary that comprises an item number 914 that uniquely identifies the chart item within the EHR system, the name 915 of the prescribed drug, the form 916 of the drug, and the date of the prescription 917. One or more of the components of the summary of the prescription 913 may act as hyperlinks to further data (not pictured) related to the chart item.

The next displayed chart item is a panel 920 of laboratory tests. The display is a summary that in the depicted embodiment of the invention comprises an item number 906, the name and date 922 of the test panel, and a code 924 indicating the status of the panel 920. The codes and their meanings depend on the embodiment of the invention, but in the depicted embodiment, the code "F" indicates that the status of the test panel 920 is "final," which means that results are available for all tests 928 comprised by the panel 920.

A panel comprises one or more laboratory tests. The panel 920 depicted in FIG. 15 comprises blood tests for glucose 930 and urea nitrogen 932, among others. In the depicted embodiment of the invention, the information for each test comprises the name 936 of the analyte, the value 938 detected by the laboratory, a "reference range" 940, which may represent a range of typical values for the analyte, and the units 942 of measurement in which the data are presented.

The panel 920 may be regarded as a single data item, as may be the prescription 913. But it comprises several tests 928, each of which may itself be regarded as a data item. The panel 920 may therefore be described as a hierarchical data item, and may be viewed either on a single line as a single data item or on multiple lines as an object comprising multiple data items. The triangle 936 is a control that toggles between the two views of the panel 920.

If, as in the depicted user interface display 890, full display of information about the attachments would exceed the available space in the attachments area 910, the attachments area 910 may contain a control 946 supporting scrolling through the displayed list of attachments.

Each data item in the attachments area 910 is associated with a checkbox control 938, by which a user may choose to save that chart item to a chart managed by that user. In an embodiment of the invention, selecting a checkbox control 938 next to a hierarchical data item may cause selection of each data item that it comprises. In such an embodiment, the user may then deselect individual data items to exclude them from the chart.

Once the user has selected one or more attached data items, the user may then select the save button 940, causing the system to save a persistent copy of each selected data item to a chart managed by the user. In such a case, an embodiment of the invention may first check that the recipient has a chart for the associated patient, and, if not, permit the recipient to create one. Creation of a patient chart by the recipient may in an embodiment rely on some or all demographic information present in the sender's version of the patient chart.

The copy is considered a persistent copy because it resides in nonvolatile storage and is not regarded by the system as a temporary file that may be subject to routine deletion.

In creating copies of attached data, an embodiment of the invention may not be limited to the one or more data sets that the reference directly specifies. An embodiment may follow references to associated data to create a copy or copies of related data, including data providing semantic data, and to associate these copies with the copy of the directly-referenced data. The embodiment may follow such links to copy associated records to any desired level of indirection. For some associated data, copying the reference to the associated data may suffice.

For example, data for a single test result may be associated with a set of data describing the data sample, a set of data describing the test panel, and/or a set of data related to payment for the test, among many other things. The result data may also be associated with information describing the vendor of laboratory services and/or the specifications for the particular test, again, among many other things. In an embodiment of the invention, copying the chart item containing such a test result may therefore comprise, e.g., copying all records specific to the test and/or patient, but copying only references to data that does not vary from test to test and/or is not specific to the particular test, panel, and patient.

In making such a copy, an embodiment of the invention has access to all data and metadata, including semantic data, that the sender has access to. Such an embodiment may thus preserve any or all such data when copying the data for the recipient.

Embodiments of the invention may comprise facilities for managing user messages. Such facilities are well known and may comprise, for example, one or more of: viewing sent or received messages; filtering messages according to one or more criteria; deleting messages, replying to messages, forwarding messages to other users; sending messages via fax; searching and/or retrieving stored messages; and/or other facilities.

We claim:

1. A method for duplicating data associated with semantic data, comprising:
    receiving an electronic message that comprises at least one reference that uniquely specifies one or more electronic records that represent a set of data, wherein the set of data comprises one or more original data items that are associated with semantic data;
    presenting the electronic message to a recipient at a first computer system;
    in response to input to the first computer system, presenting at the first computer system some or all of the data comprised by the set of data, the recipient lacking access privileges to read or copy the electronic records but for the existence of the electronic message and further lacking access privileges to read or copy the electronic records except through one or more of the references; and
    in response to further input to the first computer system, creating a persistent copy of some or all of the electronic records;
    wherein creating a persistent copy comprises creating at least one persistent electronic record that comprises a copy of at least one of the one or more original data items that are associated with semantic data, such that each copy of a data item is associated with the same semantic data that the corresponding original data item is associated with.

2. The method of claim 1, wherein each original data item comprises data related to providing health care to at least one patient.

3. A method for duplicating data, comprising:
    receiving an electronic message that comprises at least one reference that uniquely specifies one or more electronic records that represent a hierarchical data item that comprises a plurality of data items;
    presenting the electronic message to a recipient at a first computer system;
    presenting to the recipient at the first computer system a user interface comprising display of a plurality of the plurality of data items comprised by the hierarchical data item and user interface components supporting individual selection of each data item, the recipient lacking access privileges to read or copy the electronic records but for the existence of the electronic message and further lacking access privileges to read or copy the electronic records except through one or more of the references;
    in response to input to the first computer system, selecting one or more of the displayed data items; and
    in response to further input to the first computer system, creating at least one persistent electronic record that comprises a copy of each selected data item.

4. The method of claim 3, wherein:
    each data item is associated with semantic data; and
    each copy of a data item is associated with the same semantic data that the corresponding data item is associated with.

5. The method of claim 3, wherein each data item comprises data related to providing health care to at least one patient.

6. A method for duplicating data, comprising:
    receiving an electronic message that comprises at least one reference that uniquely specifies one or more electronic records that represent a collection of one or more hierarchical data items that each comprise a plurality of data items;
    presenting the electronic message to a recipient at a first computer system;
    presenting to the recipient at the first computer system a user interface comprising display of a plurality of the plurality of data items comprised by the one or more hierarchical data items and user interface components supporting individual selection of each data item, the recipient lacking access privileges to read or copy the electronic records but for the existence of the electronic message and further lacking access privileges to read or copy the electronic records except through one or more of the references;

in response to input to the first computer system, selecting one or more of the displayed data items; and in response to further input to the first computer system, creating at least one persistent electronic record that comprises a copy of each selected data item.

7. A computerized system for duplicating data associated with semantic data comprising at least one computer together with software adapted to perform one or more functions, comprising:

receiving an electronic message that comprises at least one reference that uniquely specifies one or more electronic records that represent a set of data, wherein the set of data comprises one or more original data items that are associated with semantic data;

presenting the electronic message to a recipient at a first computer system;

in response to input to the first computer system, presenting at the first computer system some or all of the data comprised by the set of data, the recipient lacking access privileges to read or copy the electronic records but for the existence of the electronic message and further lacking access privileges to read or copy the electronic records except through one or more of the references; and in response to further input to the first computer system, creating a persistent copy of some or all of the electronic records;

wherein creating a persistent copy comprises creating at least one persistent electronic record that comprises a copy of at least one of the one or more original data items that are associated with semantic data, such that each copy of a data item is associated with the same semantic data that the corresponding original data item is associated with.

8. The system of claim 7, wherein each original data item comprises data related to providing health care to at least one patient.

9. A computerized system for duplicating data comprising at least one computer together with software adapted to perform one or more functions, comprising:

receiving an electronic message that comprises at least one reference that uniquely specifies one or more electronic records that represent a hierarchical data item that comprises a plurality of data items;

presenting the electronic message to a recipient at a first computer system;

presenting to the recipient at the first computer system a user interface comprising display of a plurality of the plurality of data items comprised by the hierarchical data item and user interface components supporting individual selection of each data item, the recipient lacking access privileges to read or copy the electronic records but for the existence of the electronic message and further lacking access privileges to read or copy the electronic records except through one or more of the references;

in response to input to the first computer system, selecting one or more of the displayed data items; and in response to further input to the first computer system, creating at least one persistent electronic record that comprises a copy of each selected data item.

10. The system of claim 9, wherein:

each data item is associated with semantic data; and each copy of a data item is associated with the same semantic data that the corresponding data item is associated with.

11. The system of claim 9, wherein each data item comprises data related to providing health care to at least one patient.

12. A computerized system for duplicating data comprising at least one computer together with software adapted to perform one or more functions, comprising:

receiving an electronic message that comprises at least one reference that uniquely specifies one or more electronic records that represent a collection of one or more hierarchical data items that each comprise a plurality of data items;

presenting the electronic message to a recipient at a first computer system;

presenting to the recipient at the first computer system a user interface comprising display of a plurality of the plurality of data items comprised by the one or more hierarchical data items and user interface components supporting individual selection of each data item, the recipient lacking access privileges to read or copy the electronic records but for the existence of the electronic message and further lacking access privileges to read or copy the electronic records except through one or more of the references;

in response to input to the first computer system, selecting one or more of the displayed data items; and in response to further input to the first computer system, creating at least one persistent electronic record that comprises a copy of each selected data item.

13. A computer program product comprising computer-readable media with instructions recorded thereon, the instructions adapted to cause, when executed by at least one computer processor, at least one computer to perform one or more functions, comprising:

receiving an electronic message that comprises at least one reference that uniquely specifies one or more electronic records that represent a set of data, wherein the set of data comprises one or more original data items that are associated with semantic data;

presenting the electronic message to a recipient at a first computer system;

in response to input to the first computer system, presenting at the first computer system some or all of the data comprised by the set of data, the recipient lacking access privileges to read or copy the electronic records but for the existence of the electronic message and further lacking access privileges to read or copy the electronic records except through one or more of the references; and in response to further input to the first computer system, creating a persistent copy of some or all of the electronic records;

wherein creating a persistent copy comprises creating at least one persistent electronic record that comprises a copy of at least one of the one or more original data items that are associated with semantic data, such that each copy of a data item is associated with the same semantic data that the corresponding original data item is associated with.

14. The computer program product of claim 13, wherein each original data item comprises data related to providing health care to at least one patient.

15. A computer program product comprising computer-readable media with instructions recorded thereon, the instructions adapted to cause, when executed by at least one computer processor, at least one computer to perform one or more functions, comprising:
- receiving an electronic message that comprises at least one reference that uniquely specifies one or more electronic records that represent a hierarchical data item that comprises a plurality of data items;
- presenting the electronic message to a recipient at a first computer system;
- presenting to the recipient at the first computer system a user interface comprising display of a plurality of the plurality of data items comprised by the hierarchical data item and user interface components supporting individual selection of each data item, the recipient lacking access privileges to read or copy the electronic records but for the existence of the electronic message and further lacking access privileges to read or copy the electronic records except through one or more of the references;
- in response to input to the first computer system, selecting one or more of the displayed data items; and
- in response to further input to the first computer system, creating at least one persistent electronic record that comprises a copy of each selected data item.

16. The computer program product of claim 15, wherein:
each data item is associated with semantic data; and
each copy of a data item is associated with the same semantic data that the corresponding data item is associated with.

17. The computer program product of claim 15, wherein each data item comprises data related to providing health care to at least one patient.

18. A computer program product comprising computer-readable media with instructions recorded thereon, the instructions adapted to cause, when executed by at least one computer processor, at least one computer to perform one or more functions, comprising:
- receiving an electronic message that comprises at least one reference that uniquely specifies one or more electronic records that represent a collection of one or more hierarchical data items that each comprise a plurality of data items;
- presenting the electronic message to a recipient at a first computer system;
- presenting to the recipient at the first computer system a user interface comprising display of a plurality of the plurality of data items comprised by the one or more hierarchical data items and user interface components supporting individual selection of each data item, the recipient lacking access privileges to read or copy the electronic records but for the existence of the electronic message and further lacking access privileges to read or copy the electronic records except through one or more of the references;
- in response to input to the first computer system, selecting one or more of the displayed data items; and
- in response to further input to the first computer system, creating at least one persistent electronic record that comprises a copy of each selected data item.

* * * * *